United States Patent
Molinier Frenkel et al.

(10) Patent No.: US 11,906,520 B2
(45) Date of Patent: Feb. 20, 2024

(54) COMPOSITION AND METHODS FOR DETECTING CANCER

(71) Applicants: CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE PARIS EST CRETEIL VAL DE MARNE, Créteil (FR)

(72) Inventors: Valérie Molinier Frenkel, Saint Maur des Fossés (FR); Flavia Castellano, Antony (FR)

(73) Assignees: Centre National De La Recherche Scientifique, Paris (FR); Institut National De La Sante Et De La Rech. Med., Paris (FR); Universite Paris Est Creteil Val De Marne, Créteil (FR)

( * ) Notice: Subject to any disclaimer, the term of this patent is extended or adjusted under 35 U.S.C. 154(b) by 839 days.

(21) Appl. No.: 16/692,574

(22) Filed: Nov. 22, 2019

(65) Prior Publication Data

US 2020/0166512 A1 May 28, 2020

(30) Foreign Application Priority Data

Nov. 23, 2018 (EP) .................................. 18306563

(51) Int. Cl.
*G01N 33/574* (2006.01)
*C07K 16/24* (2006.01)

(52) U.S. Cl.
CPC ..... *G01N 33/57484* (2013.01); *C07K 16/247* (2013.01); *C07K 2317/565* (2013.01)

(58) Field of Classification Search
None
See application file for complete search history.

(56) References Cited

U.S. PATENT DOCUMENTS 5,675,063 A 10/1997 Knight
7,429,487 B2 9/2008 Pytela et al.

FOREIGN PATENT DOCUMENTS

WO 2010066858 A1 6/2010

OTHER PUBLICATIONS

Mateu et al. (Mateu MG, et. al. Eur J Immunol. Jun. 1992;22(6):1385-9) (Year: 1992).*
Greenspan et al. (Greenspan NS, Di Cera E. Defining epitopes: It's not as easy as it seems. Nat Biotechnol. Oct. 1999;17(10):936-7). (Year: 1999).*
Vajdos et al. (J Mol Biol. Jul. 5, 2002;320(2):415-28) (Year: 2002).*
Brown et al. (J Immunol. May 1996;156(9):3285-91) (Year: 1996).*
Search Report issued in corresponding European Patent Application No. 18306563 dated Apr. 11, 2019, 11 pages.
Castellano, et al. "An Overview of L-Amino Acid Oxidase Functions from Bacteria to Mammals: Focus on the Immunoregulatory Phenylalanine Oxidase IL4I1." Molecules 2017. 22(12) 2151, Dec. 5, 2017 (11 pages).
Carbonnelle-Puscian, et al. "The novel immunosuppressive enzyme IL4I1 is expressed by neoplastic cells of several B-cell Lymphomas and by tumor-associated macrophages." Leukemia. May 2009; 23 (5): pp. 952-960.
Yue, et al. "IL4I1 is a novel regulator of M2 Macrophage Polarization that can Inhibit T Cell Activation via L-Tryptophan and Arginine Depletion and IL-10 Production." PLOS one, vol. 10, No. 11. Nov. 24, 2015 (19 pages).
"Anti-IL-411/LAO antibody (ab18524) & Archived Datasheet." Abcam Catalogue. Mar. 18, 2009. URL: https://www.abcam.com/il-4i1lao-antibody-ab18524.html (6 pages).
"Anti-IL411/LAO antibody [EPR22070] (ab222102) & Datasheet." Abcam Catalogue. Jul. 31, 2018. URL: https://www.abcam.com/il-4i1lao-antibody-epr22070-ab222102.html (10 pages).

* cited by examiner

*Primary Examiner* — Brian Gangle
*Assistant Examiner* — Andrea K McCollum
(74) *Attorney, Agent, or Firm* — Pearne & Gordon LLP

(57) ABSTRACT

The invention relates to antibodies, which bind a peptide having a sequence selected from SEQ ID NO: 2, or a fragment or derivative of such an antibody having essentially the same antigen specificity. In particular, the antibodies suited to be used to detect, manage or monitor cancer in a subject, particularly cancer with interleukin-4 induced gene 1 (IL4I1) expressing cells. The invention also relates to kits or devices containing said antibodies, suitable for immunologic detection or reaction from any biological sample.

8 Claims, 7 Drawing Sheets

Figure 1:
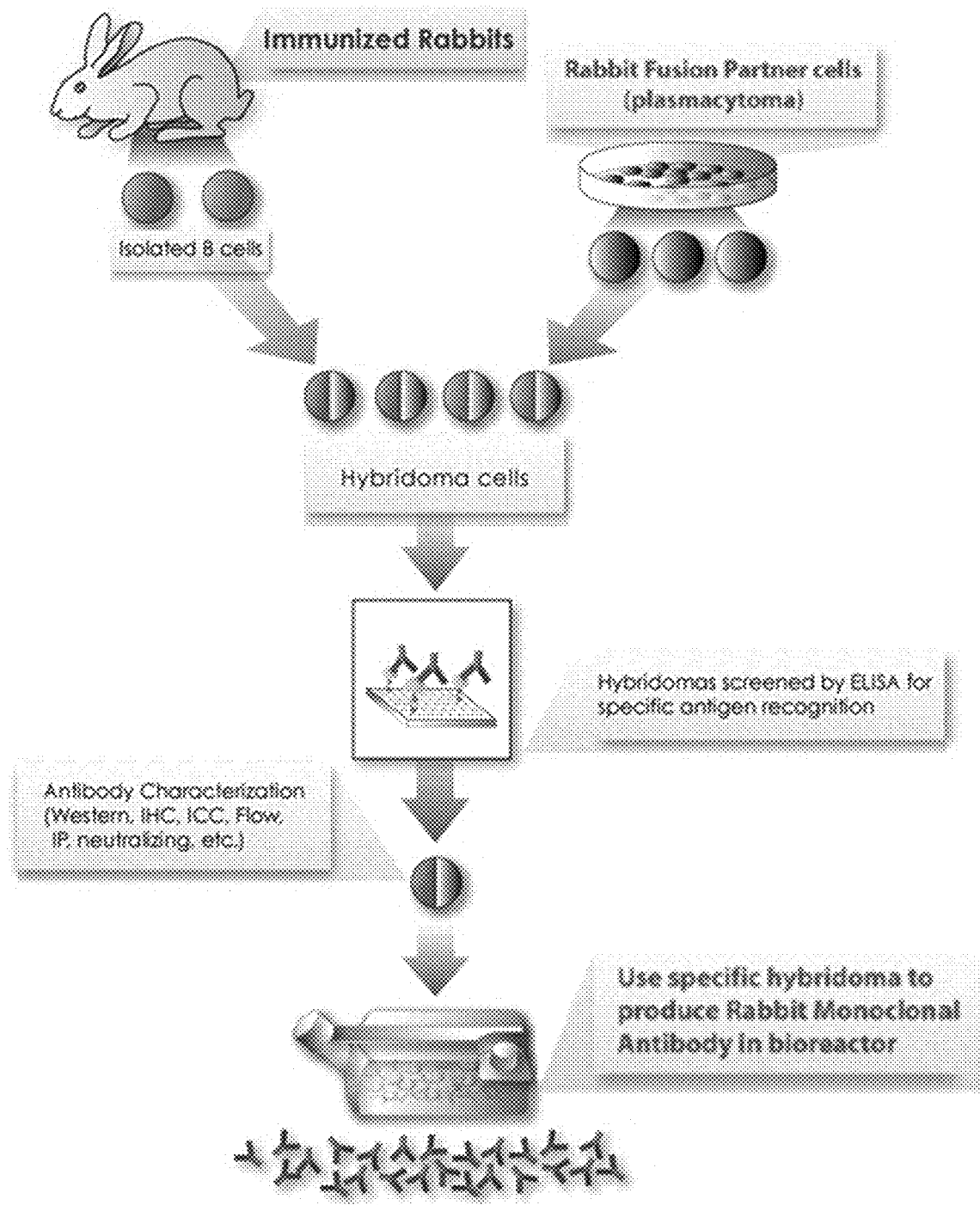
Figures 2A, 2B, 2C, 2D:
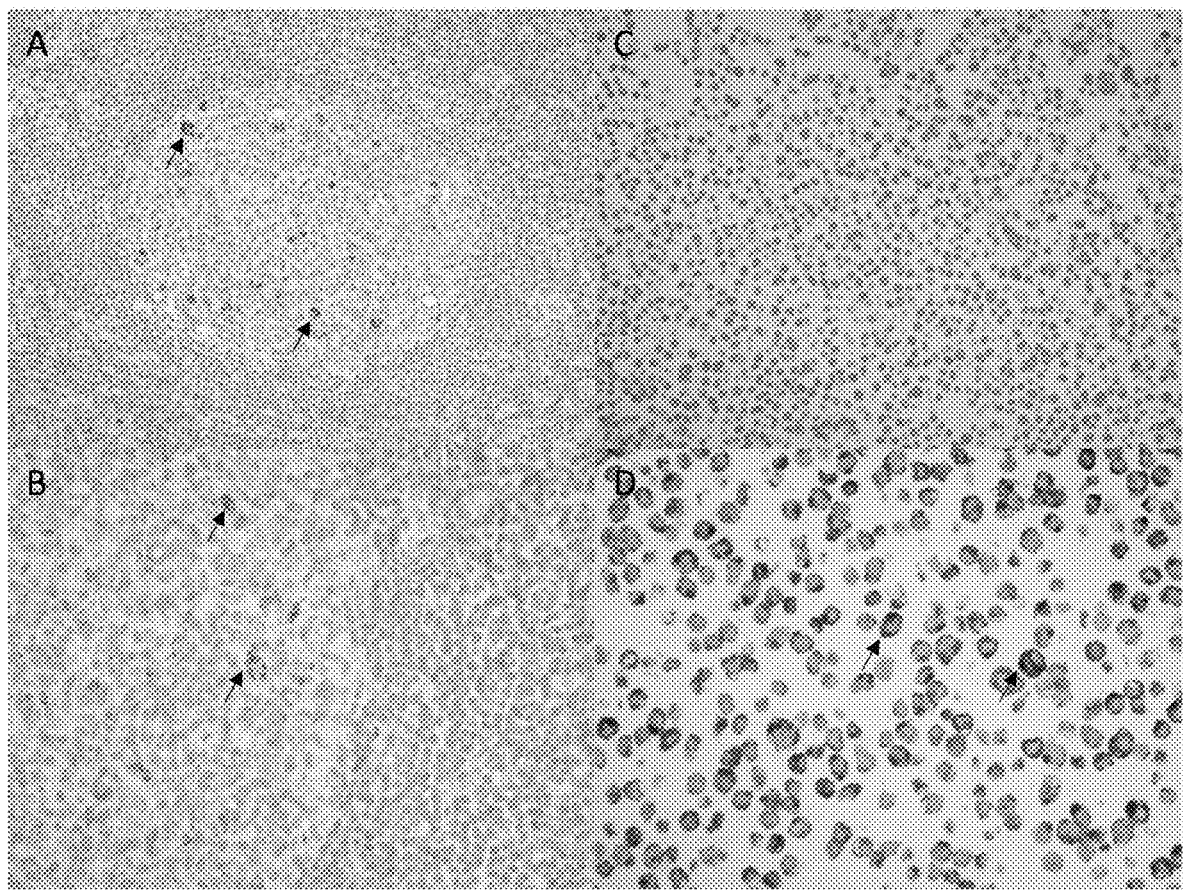
Figures 2E, 2F, 2G, 2H:
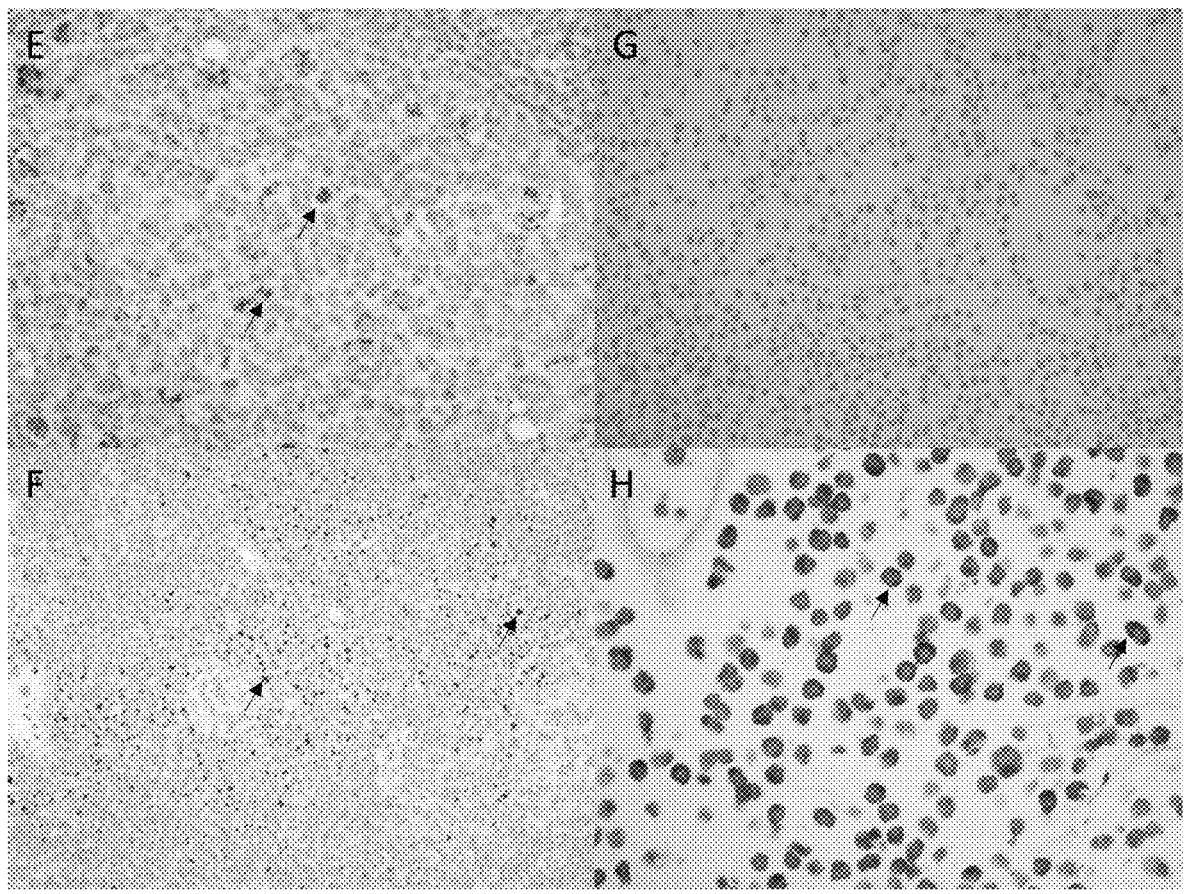
Figures 2I, 2J, 2K, 2L:
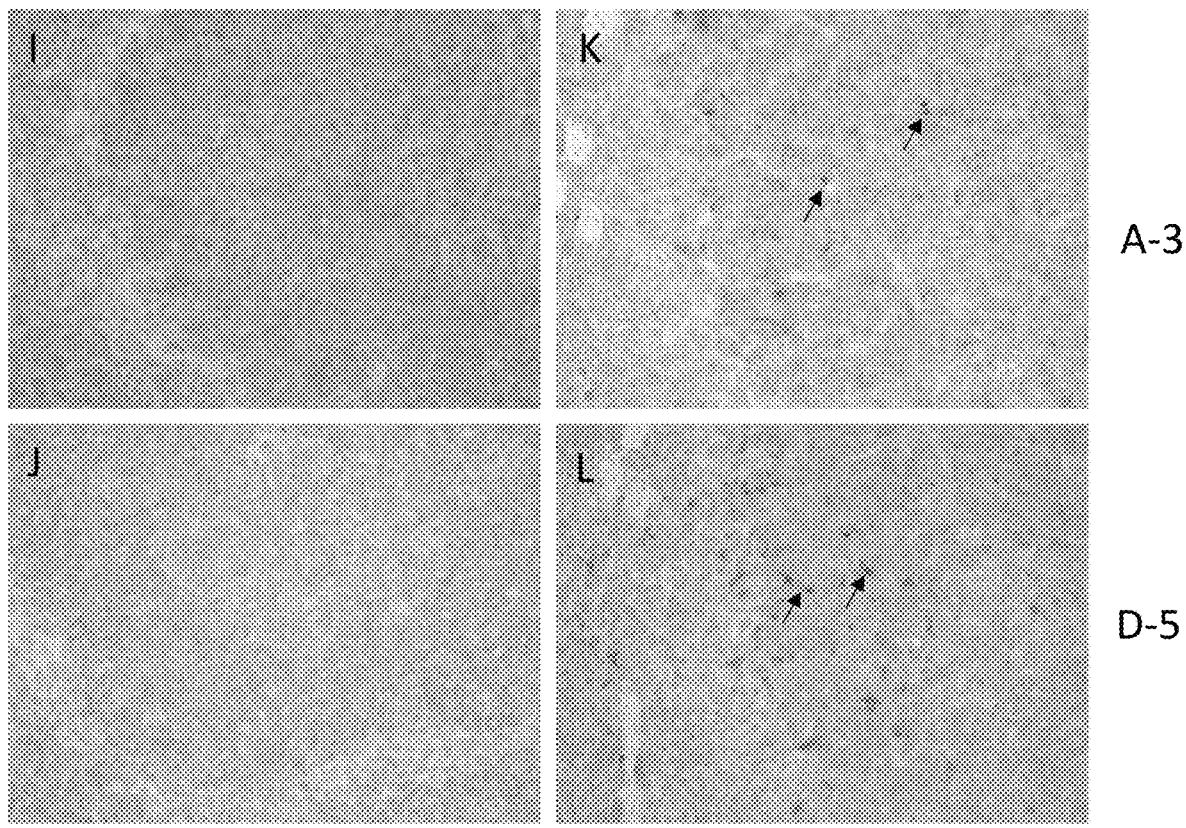

Specification includes a Sequence Listing.

SEQUENCE LISTING

<160> NUMBER OF SEQ ID NOS: 21

<210> SEQ ID NO 1
<211> LENGTH: 567
<212> TYPE: PRT
<213> ORGANISM: Homo sapiens

<400> SEQUENCE: 1

```
Met Ala Pro Leu Ala Leu His Leu Leu Val Leu Val Pro Ile Leu Leu
  1               5                  10                  15

Ser Leu Val Ala Ser Gln Asp Trp Lys Ala Glu Arg Ser Gln Asp Pro
             20                  25                  30

Phe Glu Lys Cys Met Gln Asp Pro Asp Tyr Glu Gln Leu Leu Lys Val
         35                  40                  45

Val Thr Trp Gly Leu Asn Arg Thr Leu Lys Pro Gln Arg Val Ile Val
     50                  55                  60

Val Gly Ala Gly Val Ala Gly Leu Val Ala Ala Lys Val Leu Ser Asp
 65                  70                  75                  80

Ala Gly His Lys Val Thr Ile Leu Glu Ala Asp Asn Arg Ile Gly Gly
                 85                  90                  95

Arg Ile Phe Thr Tyr Arg Asp Gln Asn Thr Gly Trp Ile Gly Glu Leu
                100                 105                 110

Gly Ala Met Arg Met Pro Ser Ser His Arg Ile Leu His Lys Leu Cys
            115                 120                 125

Gln Gly Leu Gly Leu Asn Leu Thr Lys Phe Thr Gln Tyr Asp Lys Asn
        130                 135                 140

Thr Trp Thr Glu Val His Glu Val Lys Leu Arg Asn Tyr Val Val Glu
145                 150                 155                 160

Lys Val Pro Glu Lys Leu Gly Tyr Ala Leu Arg Pro Gln Glu Lys Gly
                165                 170                 175

His Ser Pro Glu Asp Ile Tyr Gln Met Ala Leu Asn Gln Ala Leu Lys
            180                 185                 190

Asp Leu Lys Ala Leu Gly Cys Arg Lys Ala Met Lys Lys Phe Glu Arg
        195                 200                 205

His Thr Leu Leu Glu Tyr Leu Leu Gly Glu Gly Asn Leu Ser Arg Pro
    210                 215                 220

Ala Val Gln Leu Leu Gly Asp Val Met Ser Glu Asp Gly Phe Phe Tyr
225                 230                 235                 240

Leu Ser Phe Ala Glu Ala Leu Arg Ala His Ser Cys Leu Ser Asp Arg
                245                 250                 255

Leu Gln Tyr Ser Arg Ile Val Gly Gly Trp Asp Leu Leu Pro Arg Ala
            260                 265                 270

Leu Leu Ser Ser Leu Ser Gly Leu Val Leu Asn Ala Pro Val Val
        275                 280                 285

Ala Met Thr Gln Gly Pro His Asp Val His Val Gln Ile Glu Thr Ser
    290                 295                 300

Pro Pro Ala Arg Asn Leu Lys Val Leu Lys Ala Asp Val Val Leu Leu
305                 310                 315                 320

Thr Ala Ser Gly Pro Ala Val Lys Arg Ile Thr Phe Ser Pro Pro Leu
                325                 330                 335

Pro Arg His Met Gln Glu Ala Leu Arg Arg Leu His Tyr Val Pro Ala
            340                 345                 350

Thr Lys Val Phe Leu Ser Phe Arg Arg Pro Phe Trp Arg Glu Glu His
        355                 360                 365
```

```
Ile Glu Gly Gly His Ser Asn Thr Asp Arg Pro Ser Arg Met Ile Phe
    370                 375                 380
Tyr Pro Pro Arg Glu Gly Ala Leu Leu Ala Ser Tyr Thr Trp
385                 390                 395                 400
Ser Asp Ala Ala Ala Phe Ala Gly Leu Ser Arg Glu Glu Ala Leu
                405                 410                 415
Arg Leu Ala Leu Asp Asp Val Ala Ala Leu His Gly Pro Val Val Arg
                420                 425                 430
Gln Leu Trp Asp Gly Thr Gly Val Val Lys Arg Trp Ala Glu Asp Gln
            435                 440                 445
His Ser Gln Gly Gly Phe Val Val Gln Pro Pro Ala Leu Trp Gln Thr
        450                 455                 460
Glu Lys Asp Asp Trp Thr Val Pro Tyr Gly Arg Ile Tyr Phe Ala Gly
465                 470                 475                 480
Glu His Thr Ala Tyr Pro His Gly Trp Val Glu Thr Ala Val Lys Ser
                485                 490                 495
Ala Leu Arg Ala Ala Ile Lys Ile Asn Ser Arg Lys Gly Pro Ala Ser
                500                 505                 510
Asp Thr Ala Ser Pro Glu Gly His Ala Ser Asp Met Glu Gly Gln Gly
            515                 520                 525
His Val His Gly Val Ala Ser Pro Ser His Asp Leu Ala Lys Glu
        530                 535                 540
Glu Gly Ser His Pro Pro Val Gln Gly Gln Leu Ser Leu Gln Asn Thr
545                 550                 555                 560
Thr His Thr Arg Thr Ser His
                565

<210> SEQ ID NO 2
<211> LENGTH: 17
<212> TYPE: PRT
<213> ORGANISM: Homo sapiens

<400> SEQUENCE: 2

Arg Glu Glu His Ile Glu Gly Gly His Ser Asn Thr Asp Arg Pro Ser
1               5                   10                  15
Arg

<210> SEQ ID NO 3
<211> LENGTH: 111
<212> TYPE: PRT
<213> ORGANISM: Oryctolagus cuniculus

<400> SEQUENCE: 3

Glu Leu Val Leu Thr Gln Ser Pro Ser Val Ser Ala Ala Leu Gly Ala
1               5                   10                  15
Ser Ala Lys Leu Thr Cys Thr Leu Ser Ser Ala His Ser Thr Tyr Thr
                20                  25                  30
Ile Glu Trp Tyr Gln Gln Pro Gly Glu Ser Pro Tyr Leu Met
                35                  40                  45
Gln Leu Lys Ser Asp Gly Ser Tyr Thr Lys Gly Thr Gly Val Pro Asp
            50                  55                  60
Arg Phe Ser Gly Ser Ser Ser Gly Ala Asp Arg Tyr Leu Ile Ile Phe
65                  70                  75                  80
Ser Val Gln Ala Asp Asp Glu Ala Asp Tyr Tyr Cys Gly Ala Asn Tyr
                85                  90                  95
Ser Ser Gly Tyr Val Phe Gly Gly Gly Thr Gln Leu Thr Val Thr
```

```
                   100                 105                 110

<210> SEQ ID NO 4
<211> LENGTH: 126
<212> TYPE: PRT
<213> ORGANISM: Oryctolagus cuniculus

<400> SEQUENCE: 4

Gln Gln Gln Leu Val Glu Ser Gly Gly Asp Leu Val Lys Pro Glu Gly
1               5                   10                  15

Ser Leu Thr Leu Thr Cys Thr Ala Ser Gly Phe Ser Leu Ser Ala Gly
            20                  25                  30

Tyr Phe Ile Cys Trp Ile Arg Gln Ala Pro Gly Lys Gly Leu Glu Trp
        35                  40                  45

Ile Gly Ser Val Phe Ser Gly Ser Ser Gly Thr Thr Tyr Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Ile Tyr Phe
                85                  90                  95

Cys Ala Arg Gly Gly Val Leu Gly Gly Arg Val Ala Tyr Asp Asn Ser
            100                 105                 110

Phe Asp His Trp Gly Pro Gly Thr Leu Val Thr Val Ser Ser
        115                 120                 125

<210> SEQ ID NO 5
<211> LENGTH: 7
<212> TYPE: PRT
<213> ORGANISM: Oryctolagus cuniculus

<400> SEQUENCE: 5

Ser Ala His Ser Thr Tyr Thr
1               5

<210> SEQ ID NO 6
<211> LENGTH: 7
<212> TYPE: PRT
<213> ORGANISM: Oryctolagus cuniculus

<400> SEQUENCE: 6

Leu Lys Ser Asp Gly Ser Tyr
1               5

<210> SEQ ID NO 7
<211> LENGTH: 9
<212> TYPE: PRT
<213> ORGANISM: Oryctolagus cuniculus

<400> SEQUENCE: 7

Gly Ala Asn Tyr Ser Ser Gly Tyr Val
1               5

<210> SEQ ID NO 8
<211> LENGTH: 9
<212> TYPE: PRT
<213> ORGANISM: Oryctolagus cuniculus

<400> SEQUENCE: 8

Gly Phe Ser Leu Ser Ala Gly Tyr Phe
1               5
```

<210> SEQ ID NO 9
<211> LENGTH: 9
<212> TYPE: PRT
<213> ORGANISM: Oryctolagus cuniculus

<400> SEQUENCE: 9

Val Phe Ser Gly Ser Ser Gly Thr Thr
1               5

<210> SEQ ID NO 10
<211> LENGTH: 18
<212> TYPE: PRT
<213> ORGANISM: Oryctolagus cuniculus

<400> SEQUENCE: 10

Ala Arg Gly Gly Val Leu Gly Gly Arg Val Ala Tyr Asp Asn Ser Phe
1               5                   10                  15

Asp His

<210> SEQ ID NO 11
<211> LENGTH: 333
<212> TYPE: DNA
<213> ORGANISM: Oryctolagus cuniculus

<400> SEQUENCE: 11
gagctcgtgc tgactcagtc gccctctgtg tctgccgccc tgggagcctc tgccaagctc    60
acctgcaccc tgagcagtgc ccacagcacc tacaccattg aatggtatca gcagcagcca   120
ggggagtccc ctcggtacct gatgcagctt aagagtgatg aagctacac taagggggacc   180 ggggtccctg atcgcttctc gggctccagc tctggggctg accgctactt gatcatcttc   240
agcgtccagg ctgatgacga agccgactac tattgtggtg caaattatag tagtggatat   300
gtgttcggcg gagggaccca gctgaccgtc aca                                333

<210> SEQ ID NO 12
<211> LENGTH: 378
<212> TYPE: DNA
<213> ORGANISM: Oryctolagus cuniculus

<400> SEQUENCE: 12
cagcagcagc tggtggagtc cggggggagac ctggtcaagc ctgagggatc cctgacactc    60
acctgcacag cctctggatt ctccttaagt gccggctact tcatatgctg gatccgccag   120
gctccaggga aggggctgga gtggatcgga tccgttttta gtgggagtag tggtaccact   180
tactacgcga gctgggcgaa aggccgattc accatctcca aaacctcgtc gaccacggtg   240
actctgcaaa tgaccagtct gacagccgcg gacacggcca tctatttctg tgcgaggggg   300
ggtgttcttg gtggtcgtgt tgcatatgac aactctttttg atcactggggg cccaggcacc   360 ctggtcaccg tctcctca                                                  378

<210> SEQ ID NO 13
<211> LENGTH: 115
<212> TYPE: PRT
<213> ORGANISM: Oryctolagus cuniculus

<400> SEQUENCE: 13

Glu Leu Val Leu Thr Gln Ser Pro Ser Val Ser Ala Ala Leu Gly Ala
1               5                   10                  15

Ser Ala Lys Leu Thr Cys Thr Leu Ser Ser Ala His Ser Thr Tyr Thr
            20                  25                  30

```
Ile Asp Trp Tyr Gln Gln Pro Gly Glu Ser Pro Arg Tyr Leu Met
         35                  40                  45
Gln Leu Lys Ser Asp Gly Thr Tyr Thr Lys Gly Thr Gly Val Pro Asp
 50                  55                  60
Arg Phe Ser Gly Ser Ser Gly Ala Asp Arg Tyr Leu Ile Ile Pro
 65                  70                  75                  80
Ser Val Gln Ala Asp Asp Glu Ala Gly Tyr Tyr Cys Gly Ala Asn Tyr
                 85                  90                  95
Ser Gly Gly Tyr Val Phe Gly Gly Gly Thr Gln Leu Thr Val Thr Arg
                100                 105                 110
Thr Val Ala
        115

<210> SEQ ID NO 14
<211> LENGTH: 7
<212> TYPE: PRT
<213> ORGANISM: Oryctolagus cuniculus

<400> SEQUENCE: 14

Leu Lys Ser Asp Gly Thr Tyr
1               5

<210> SEQ ID NO 15
<211> LENGTH: 9
<212> TYPE: PRT
<213> ORGANISM: Oryctolagus cuniculus

<400> SEQUENCE: 15

Gly Ala Asn Tyr Ser Gly Gly Tyr Val
1               5

<210> SEQ ID NO 16
<211> LENGTH: 345
<212> TYPE: DNA
<213> ORGANISM: Oryctolagus cuniculus

<400> SEQUENCE: 16
gagctcgtgc tgactcagtc gccctctgtg tctgccgccc tgggagcctc tgccaagctc     60
acctgcaccc tgagcagtgc ccacagcacc tacaccattg actggtatca gcagcagcca    120
ggggagtccc ctcggtacct gatgcagctt aagagtgatg gaacttacac caaggggacc    180
ggggtccctg atcgcttctc gggctccagc tccggggctg accgctactt gatcatcccc    240
agcgtccagg ctgatgacga agccggctac tattgtggtg caaattatag cggtgggtat    300
gtgttcggcg gagggaccca gctgaccgtc acacgaactg tggct                    345

<210> SEQ ID NO 17
<211> LENGTH: 17
<212> TYPE: PRT
<213> ORGANISM: Mus musculus

<400> SEQUENCE: 17

His Glu Glu His Ile Glu Gly Gly His Ser Asn Thr Asp Arg Pro Ser
1               5                   10                  15

Arg

<210> SEQ ID NO 18
<211> LENGTH: 9
<212> TYPE: PRT
<213> ORGANISM: Oryctolagus cuniculus
```

```
<400> SEQUENCE: 18

Ile Phe Ser Gly Ser Ser Gly Ser Thr
1               5

<210> SEQ ID NO 19
<211> LENGTH: 18
<212> TYPE: PRT
<213> ORGANISM: Oryctolagus cuniculus

<400> SEQUENCE: 19

Ala Arg Gly Gly Val Val Asp Gly Arg Val Ala Tyr Asp Asn Ser Phe
1               5                   10                  15

Asp His

<210> SEQ ID NO 20
<211> LENGTH: 375
<212> TYPE: DNA
<213> ORGANISM: Oryctolagus cuniculus

<400> SEQUENCE: 20
cagtcgttgg aggagtccgg gggagacctg gtcaagcctg agggatccct gacactcacc      60
tgcacagcct ctggattctc cttaagtgcc ggctacttca tgtgctgggt ccgccaggct     120
ccagggaagg gctggagtg  gatcggatcc attttagtg  gtagtagtgg tagtacttac     180
tacgcgagct gggcgaaagg ccgattcacc atctccaaaa cctcgtcgac cacggtgact     240
ctgcaaatga ccagtctgac agccgcggac acggccatct atttctgtgc gaggggggt     300 gttgttgatg gtcgtgttgc atatgacaac tcttttgatc actggggccc aggcaccctg     360
gtcaccgtct cctca                                                      375

<210> SEQ ID NO 21
<211> LENGTH: 125
<212> TYPE: PRT
<213> ORGANISM: Oryctolagus cuniculus

<400> SEQUENCE: 21

Gln Ser Leu Glu Glu Ser Gly Gly Asp Leu Val Lys Pro Gly Ser
1               5                   10                  15

Leu Thr Leu Thr Cys Thr Ala Ser Gly Phe Ser Leu Ser Ala Gly Tyr
                20                  25                  30

Phe Met Cys Trp Val Arg Gln Ala Pro Gly Lys Gly Leu Glu Trp Ile
                35                  40                  45

Gly Ser Ile Phe Ser Gly Ser Ser Gly Ser Thr Tyr Tyr Ala Ser Trp
50                  55                  60

Ala Lys Gly Arg Phe Thr Ile Ser Lys Thr Ser Ser Thr Val Thr
65                  70                  75                  80

Leu Gln Met Thr Ser Leu Thr Ala Ala Asp Thr Ala Ile Tyr Phe Cys
                85                  90                  95

Ala Arg Gly Gly Val Val Asp Gly Arg Val Ala Tyr Asp Asn Ser Phe
                100                 105                 110

Asp His Trp Gly Pro Gly Thr Leu Val Thr Val Ser Ser
            115                 120                 125
```

COMPOSITION AND METHODS FOR DETECTING CANCER

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "APIC-61083-Sequence-Listing_ST25.txt", created Nov. 21, 2019, file size of 16,384 bytes, is hereby incorporated by reference.

FIELD OF THE INVENTION

The present invention relates to the field of medicine, in particular of oncology. Especially, the invention relates to compositions and methods for detecting, managing, monitoring, imaging, diagnosis of various cancers, as well as for drug development. The present invention is particularly suited for detecting, managing or monitoring cancer with IL4I1-expressing cells.

BACKGROUND OF THE INVENTION

L-amino acid oxidases (LAAOs) are flavin adenine dinucleotide-dependent enzymes present in all major kingdom of life, from bacteria to mammals. They participate in defense mechanisms by limiting the growth of most bacteria and parasites. A few mammalian LAAOs have been described, of which the enzyme "interleukin-4 induced gene 1" (IL4I1) is the best characterized. The secreted IL4I1 (interleukin-4-induced gene 1) enzyme catabolizes L-phenylalanine and to a lesser extent arginine to generate hydrogen peroxide ($H_2O_2$), ammonia ($NH_3$) and the corresponding a-keto acid. (Castellano and Molinier-Frenkel. 2017)

In most cancer patients, IL4I1 is expressed either by tumor cells themselves (e.g., some B cell lymphoma subsets, mesothelioma or ovarian cancer) or by tumor-associated macrophages (TAM) or dendritic cells (DC) (Carbonnelle-Puscian et al. 2009). It is a secreted enzyme physiologically produced by antigen presenting cells (APC) of the myeloid and B cell lineages and T helper type (Th) 17 cells. Important roles of IL4I1 in the fine control of the adaptive immune response in mice and humans have emerged during the last few years. Indeed, IL4I1 inhibits T cell proliferation and cytokine production and facilitates naive $CD4^+$ T-cell differentiation into regulatory T cells in vitro by limiting the capacity of T lymphocytes to respond to clonal receptor stimulation. It also plays a role in controlling the germinal center reaction for antibody production and limits Th1 and Th17 responses. No routinely used diagnostic method currently allows to discriminate between IL4I1-expressing and non-expressing cancers. Commercially available antibodies that recognize IL4I1 are poorly characterized polyclonal rabbit antibodies that lack sensitivity and specificity. Quantification of IL4I1 expression in cancer patients could be useful in the prognosis evaluation, since the enzyme facilitates tumor growth by inhibiting the anti-tumor T-cell response. Furthermore, due to these immunosuppressive properties IL4I1 represents a new potential druggable target in the field of immunomodulation in cancer. Accordingly, there is a need for tools which can be associated with drug development.

In that context, it was notably disclosed methods for determining the prognosis or the responsiveness of a subject suffering from cancer and agents with IL4I1 inhibitory activity in WO2010/066858, including antibody against IL4I1 or a fragment thereof which binds IL4I1 and wherein said antibody against IL4I1 or fragment thereof inhibits IL4I1 enzymatic activity. However, the antibody used was a polyclonal rabbit antibody commercialized by Abcam (reference Ab18524, Cambridge, UK) although it is rather not satisfactory because it needs repeated immunization of the animals and its properties may vary from batch to batch due to variability in the immune response of the animals. Moreover, its sensitivity and specificity were limited due to its polyclonal nature, thus limiting its use in the detection, the management, the monitoring, the imaging or as diagnostics tool. The antibodies developed by the inventors are clonal and validation of their recognition properties has shown that they are highly specific and sensitive.

Further, many antibodies against IL4I1 are disclosed in the background art (see Table 1 below). Antibodies described below have been obtained using various immunogens, including the whole protein and N-terminal and C-terminal peptides, some of which are not clearly defined in the available description (see Table 1).

TABLE 1

Antibodies against IL4I1 commercially available.

| Company | Type | Species Reactivity | Technique | Validation | Antibody | Target Region |
|---|---|---|---|---|---|---|
| Abcam | Rabbit polyclonal | human | WB, IHC, IF | IF on Hela, WB on testis | Ab18524 | Synthetic peptide residues 350-450 of Human IL4I1. |
| Biomatik | Rabbit polyclonal | Human, mouse | ELISA, WB, IHC, IF | No data | CAC07670 | No data |
| Aviva/Invitrogen/ Origene | Rabbit polyclonal | Human | WB | WB Human Hela (transfected! | ARP65454_P050 | C-terminal PHGWVETAVKSALRAAI KINSRKGPASDTASPEGH ASDMEGQGHVHGVAS (SEQ ID NO: 1 (residues 486-535)) |
| Aviva/Abclonal tech/Gentex/St John's Laboratory/ Raybiotech | Rabbit polyclonal | Human, mouse, rat | WB | WB, cell lines, rat, mouse testis | OAAN02717 | Recombinant (whole!) human protein |

TABLE 1-continued

Antibodies against IL4I1 commercially available.

| Company | Type | Species Reactivity | Technique | Validation | Antibody | Target Region |
|---|---|---|---|---|---|---|
| Aviva | Rabbit polyclonal | Human | WB, ELISA | No data | OASG03841 | N-terminal region peptide (no precision) |
| Aviva | Rabbit polyclonal | Human, mouse | ELISA, WB, IHC, IF | IHC hu prostate cancer, WB mouse stomach tissue | OACA09657 | Recombinant human protein (139-339AA) |
| ProSci, Inc/NSJ Bioreagent/United States Biological | Rabbit polyclonal | Human | WB | Western Blot Hela and HT-1080 whole cell lysates | 61-234 | KLH conjugated synthetic peptide between 391-422 amino acids from hu IL4I1 |
| MyBioSource.com/ Biobyt/lnvitrogen/ Origene | Rabbit polyclonal | Human | WB, ELISA (EIA) | WB Hela without precisions | MBS853867 | Synthesized peptide from N-terminal human IL4I1 |
| Biobyt | Rabbit polyclonal | Human, Mouse, Rat | WB IHC-P, P-ELISA | IHC rat kidney, rat spleen, WB mouse kidney. | orb100203 | KLH conjugated synthetic peptide derived between 61-150 amino acids of human IL4I1 |
| Abbexa | Rabbit polyclonal | Human, Mouse, Rat | WB | No data | abx006138 | No data |
| Bioss antibodies | Rabbit polyclonal | Human, Mouse, Rat | WB, IHC-P, IF(IHC-P) | WB: spleen (negative), kidney (positive)! IHC rat kidney | bs-6841R | KLH conjugated synthetic peptide derived from human IL-4I1 (Range 50-100/567) |

As listed in Table 1, the activities of these commercially available antibodies are poorly characterized, sometimes the data are even contradictory with known data of IL4I1 expression, indicating that they have not been validated and might be unspecific and/or not sensitive.

Thus, these antibodies are not satisfactory enough to be used in the detection, the management, the monitoring, the imaging or in diagnostic tools.

Therefore, there is a need for more effective sensitivity and specificity for detecting, managing, monitoring, imaging, diagnosis of various cancers, as well as for drug development, especially in the diagnosis of cancer with IL4I1 (Interleukin 4 Induced gene 1) expressing cells, which are present in a large set of human cancers.

SUMMARY OF THE INVENTION

The inventors surprisingly found that the antibodies which bind the specific region 365-381 (SEQ ID NO:2) in IL4I1 protein improved significantly the results compared to antibodies disclosed until now.

TABLE 2

Sequence of IL4I1 protein Wild Type.

(SEQ ID NO: 1)
MAPLALHLLVLVPILLSLVASQDWKAERSQDPFEKCMQDPDYEQLLKVVTVVGLNRTLKPQRVIVVGAGVAGLVAAKVL

SDAGHKVTILEADNRIGGRIFTYRDQNTGWIGELGAMRMPSSHRILHKLCQGLGLNLTKFTQYDKNTWTEVHEVKLRN

YVVEKVPEKLGYALRPQEKGHSPEDIYQMALNQALKDLKALGCRKAMKKFERHTLLEYLLGEGNLSRPAVQLLGDVMSE

DGFFYLSFAEALRAHSCLSDRLQYSRIVGGWDLLPRALLSSLSGLVLLNAPVVAMTQGPHDVHVQIETSPPARNLKVLKA

DVVLLTASGPAVKRITFSPPLPRHMQEALRRLHYVPATKVFLSFRRPFWREEHIEGGHSNTDRPSRMIFYPPPREGALLLA

SYTWSDAAAAFAGLSREEALRLALDDVAALHGPVVRQLWDGTGVVKRWAEDQHSQGGFVVQPPALWQTEKDDWT

TABLE 2-continued

Sequence of IL4I1 protein Wild Type.

```
VPYGRIYFAGEHTAYPHGWVETAVKSALRAAIKINSRKGPASDTASPEGHASDMEGQGHVHGVASSPSHDLAKEEGSH
PPVQGQLSLQNTTHTRTSH
```

In a first aspect, the invention relates to particular antibodies, which bind a peptide having a sequence selected from SEQ ID NO: 2 (REEHIEGGHSNTDRPSR), or a fragment or derivative of such an antibody having essentially the same antigen specificity.

The antibodies, either alone or in combination, can be used to detect, manage or monitor cancer in a subject, particularly cancer with IL4I1-expressing cells. The invention also relates to kits or devices containing said antibodies, suitable for immunologic detection or reaction from any biological sample. Further, the invention relates to hybridoma cells producing said antibodies and method of production thereof.

In a second aspect, the invention relates to a method for detecting, monitoring, managing, imaging or diagnosing a cancer in a subject, wherein the cancer to be treated displays IL4I1-expressing cells and the subject displays an IL4I1-positive status. The invention also relates to a method for determining the chances of a patient suffering from IL4I1-positive cancer, to respond to a treatment comprising the administration of an IL4I1 inhibitor.

The invention is particularly suited to detect cancers with IL4I1-expressing cells.

LEGEND OF DRAWING

FIG. 1. The major step of the monoclonal antibody process.

FIGS. 2A through 2L. Immunohistochemistry on human samples. A reactive lymph node (FIGS. 2A, 2B, 2E, 2F), untransfected HEK293 cells (FIGS. 2C, 2G) and HEK293 transfected with human-IL4I1 cDNA (FIGS. 2D, 2H) or IL4I1 KO mouse spleens (FIGS. 2I, 2J) or WT mouse spleens (FIGS. 2K, 2L) were stained with the anti-IL4I1 antibody, clone A-3 (FIGS. 2A, 2B, 2C, 2D, 2I, 2K) at a dilution of 1.5 µg/mL or with clone D-5 (FIGS. 2E, 2F, 2G, 2H, 2J, 2L) at a dilution of 470 ng/mL. Specific IL4I1 staining was followed by amplification with anti-rabbit HRP antibody and revelation with the ENVision HRP system. IL4I1 labeling appears as brown dots as indicated by black arrows. FIGS. 2A, 2C, 2F, 2G are at 20× magnification, while FIGS. 2B, 2D, 2E, 2H, 2I, 2J, 2K, 2L are at 40× magnification.

Figure 3A:
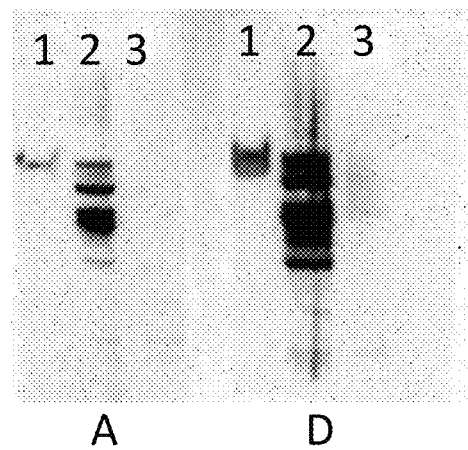
Figure 3B:
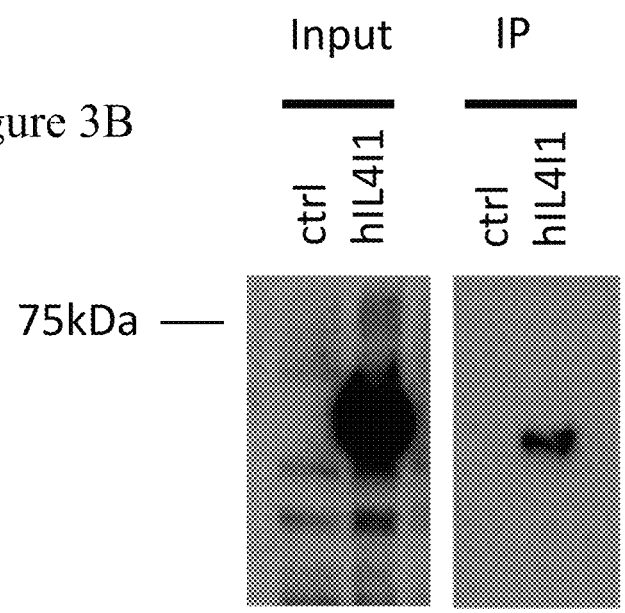

FIGS. 3A through 3B. Western blot (WB) and immunoprecipitation (IP). FIG. 3A: WB on medium and cell lysates. Medium (Lane 1) or cell lysates from HEK293 cells transfected with a vector expressing human myc-tagged IL4I1 after tetracycline induction for 48 h (Lane 2) or HEK293 cells transfected with an empty vector (Lane 3) were separated on a 10% SDS-PAGE and blotted onto PVDF. Blots were revealed with anti-IL4I1 hybridoma supernatant from clone A-3(left) and clone D-5 (right) followed by anti-rabbit-HRP antibody and ECL. Images were taken using the AUTOCHEMI imager (UVP, UK) using the LABWORKS software. FIG. 3B: IL4I1 IP using hybridoma clone D-5. HEK293 cells transfected with a vector expressing human myc-tagged IL4I1 after tetracycline induction, or empty vector controls were lysed and immunoprecipitated with the hybridoma supernatant of clone D-5, followed by protein A/G agarose separation. Immunoprecipitates and initial lysates (inputs) were separated on a 10% SDS-PAGE and blotted onto PVDF. Blots were revealed with an anti-myc antibody (clone 9E10).

Figure 4:
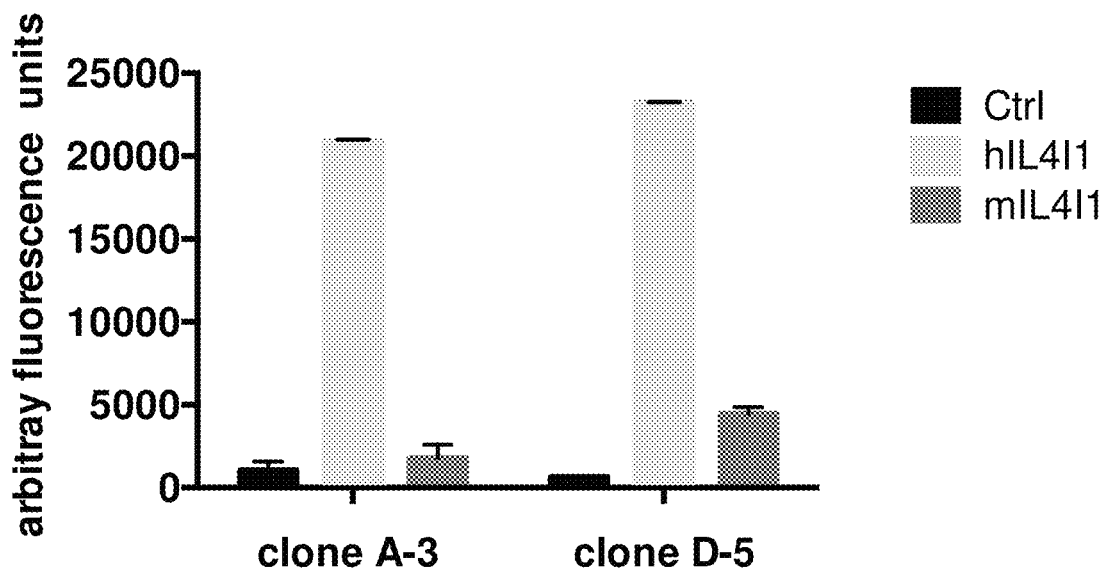

FIG. 4. IL4I1 detection by single layer ELISA. Human (hIL4I1) and mouse (mIL4I1) IL4I1 recombinant proteins were absorbed on 96 well plates and revealed using clone A-3 hybridoma supernatant or clone D-5 hybridoma supernatant (dilution 1:6), followed by amplification with anti-rabbit HRP antibody and revelation with a fluorometric substrate.

Figure 5:
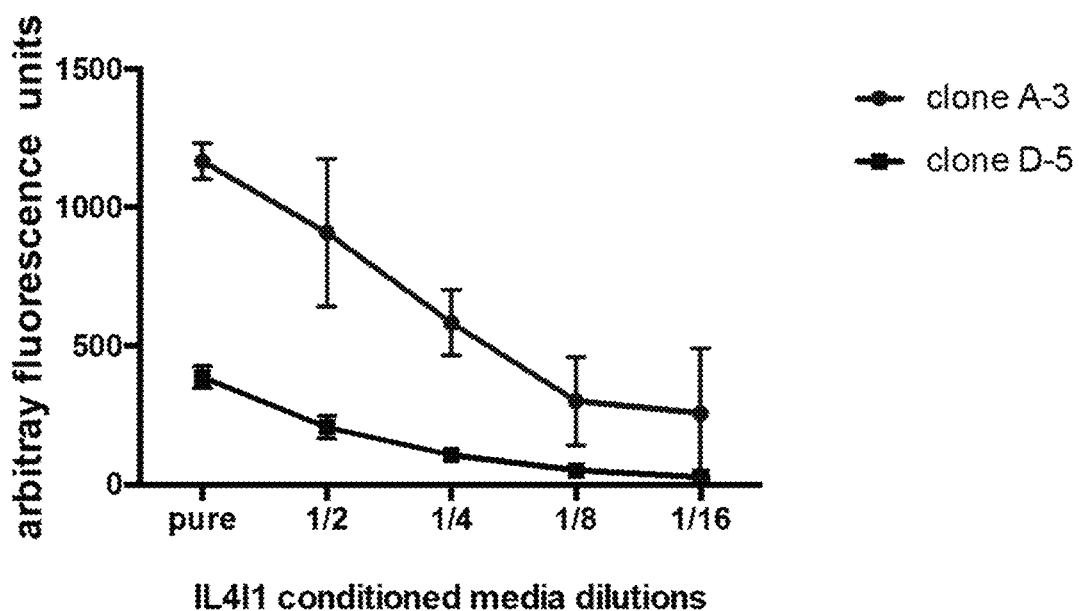
Figure 6A:
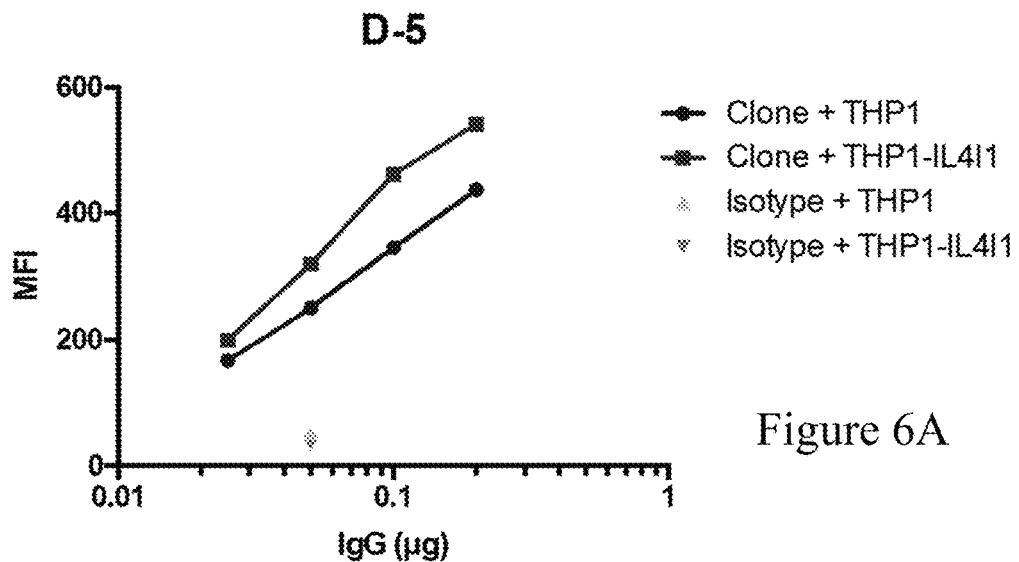
Figure 6B:
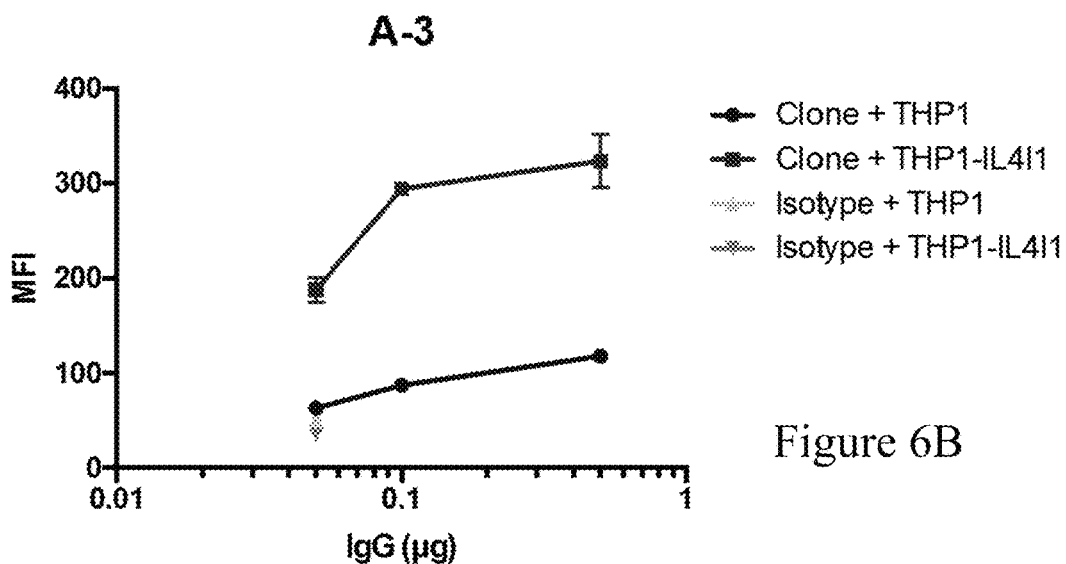
Figure 6C:
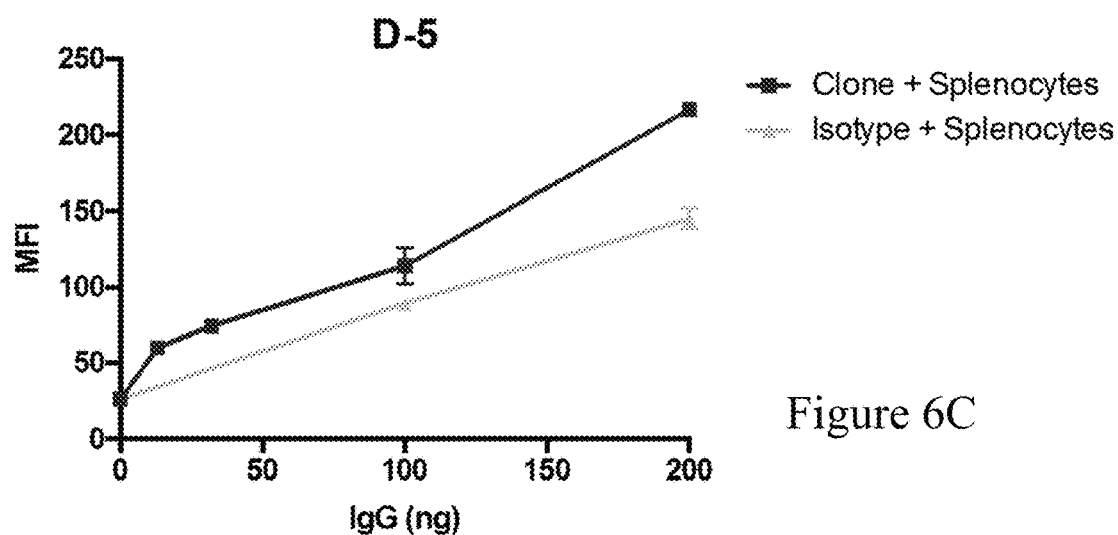

FIG. 5. IL4I1 detection by sandwich ELISA. Anti-IL4I1 hen capture antibody (produced by the inventors) was adsorbed on 96 well plates. Conditioned media containing human recombinant IL4I1 serially diluted in PBS were added. Specific fixation of IL4I1 was revealed with either purified IgG from clone A-3 or clone D-5, followed by fluorometric detection as in FIG. 4. Values are the mean of quadruplicate values±SD FIGS. 6A through 6C. IL4I1 detection by flow cytometry. FIGS. 6A and 6B: THP1 cells and recombinant THP1 cells stably transfected with an IL4I1 coding vector were permeabilized before incubation with increasing doses of purified IgG from clone D-5 (A) or A-3 (B) or a fixed dose of rabbit IgG (isotype control), followed by revelation with an anti-rabbit conjugated with ALEXA FLUOR 488 dye. FIG. 6C: Mouse splenocytes were incubated with increasing doses of purified IgG from clone D-5 or a fixed dose of rabbit IgG (isotype control), followed by revelation with an anti-rabbit conjugated with ALEXA FLUOR 488 dye. Data were acquired on a CYAN flow cytometer (Dako) and analyzed using the FLOWJO software.

DETAILED DESCRIPTION OF THE INVENTION

Definition

As intended herein, the term "comprising" has the meaning of "including" or "containing", which means that when an object "comprises" one or several elements, other elements than those mentioned may also be included in the object. In contrast, when an object is said to "consist of" one or several elements, the object cannot include other elements than those mentioned.

The term "IL4I1" refers to Interleukin 4-induced gene 1 and encodes a protein with high homology to L-amino acid oxidase which contains the conserved amino acids thought to be involved in catalysis and binding of flavin adenine dinucleotide (FAD) cofactor. IL4I1 is also known as "FIG. 1" and was initially isolated in a screen for IL4-induced genes from mouse B cells using cDNA representational difference analysis. This protein corresponds to isoform 1, whose expression is restricted to lymphoid tissues. A second isoform was described in rare cells of nervous tissue (e.g., Purkinje cells) and of the testis (Sertoli cells) and three other isoforms have been referenced in databases. All these isoforms differ in the first exons encoding their respective signal peptides that should be cleaved at homologous positions in the proteins. Consequently, the five proteins should have identical sequences once processed. IL4I1 (isoform 1) has been detected in several cells of the immune system depending on the inducing stimuli. Apart from B cells, IL4I1 can be expressed by monocytes, macrophages, dendritic cells (DC) and T cells. IL4I1 can also be occasionally expressed by neoplastic B cells and non-lymphoid tumor cells. IL4I1 may play an important immunosuppressive role in several human conditions, including cancer, as it has been shown to regulate T-cell and B-cell properties both in vitro and in vivo. The term "anti-IL4I1" refers to an antibody directed against IL4I1.

According to the present invention, "antibody" or "immunoglobulin" have the same meaning and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments.

In the basal structure of most mammalian antibodies, including rabbit antibodies, two heavy chains are linked to each other by disulfide bonds and each heavy chain is linked to a light chain by a disulfide bond. Humans and mice have five antibody isotypes (IgA, IgD, IgE, IgG, and IgM) which determine the functional activity of an antibody molecule. So far, four isotypes have been identified (IgA, IgE, IgG, and IgM) in rabbits. There are two types of light chain, lambda (λ) and kappa (κ) in humans. Moreover, rabbits have two K light chain types κ1 and κ2. Most of rabbit research antibodies are of IgG isotype. Each chain contains distinct sequence domains. The light chain includes two domains, a variable domain (VL) and a constant domain (CL). The IgG heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant (epitope). Antibody combining sites are made up of residues that are primarily from the hypervariable or complementarity determining regions (CDRs). Occasionally, residues from no hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each has three CDRs, designated L-CDR1, L-CDR2, LCDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an anti-IL4I1 antibody, and a CH domain and a CL domain of a human antibody. According to the invention, the term "humanized antibody" refers to an antibody having variable region framework and constant regions from a human antibody but retains the CDRs of an anti-IL4I1 antibody. The term "Fab" denotes an antibody fragment having a molecular weight of about 50,000 Da and antigen binding activity, in which about a half of the N-terminal side of H chain and the entire L chain, among fragments obtained by treating IgG with a protease, papain, are bound together through a disulfide bond. The term "F(ab')2" refers to an antibody fragment having a molecular weight of about 100,000 Da and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 Da and antigen binding activity, which is obtained by cutting a disulfide bond of the hinge region of the F(ab')2. A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilized by a disulfide bond. Divalent and multivalent antibody fragments can form either spontaneously by association of monovalent scFvs, or can be generated by coupling monovalent scFvs by a peptide linker, such as divalent sc(Fv)2. The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

According to the invention, the terms "subject", "individual", and "patient" are used interchangeably herein and refer to a mammal affected or likely to be affected with disease associated with overexpression of IL4I1 being, more precisely a mammal suffering from cancer associated with overexpression of IL4I1. Subjects are preferably humans.

Antibodies of the Invention

The present invention provides isolated anti-IL4I1 antibodies or fragments thereof. These antibodies are specific to the amino acid sequence REEHIEGGHSNTDRPSR (SEQ ID NO: 2). Furthermore, Inventors have found that these new antibodies are particularly suitable for detecting IL4I1, especially when compared to the antibodies of the art. According to the first aspect of the invention, the antibodies bind a peptide having the amino acid sequence REE- HIEGGHSNTDRPSR (SEQ ID NO: 2), or a fragment or derivative of such an antibody having essentially the same antigen specificity.

Alternately, the present invention relates to an antibody, fragment or derivative, which binds a polypeptide comprising the peptide sequence REEHIEGGHSNTDRPSR (SEQ ID NO: 2).

Unexpectedly, the inventors found that an antibody binding a peptide which is not a peptide located in the FAD binding Region of IL4I1 protein is beneficial to provide an anti-IL4I1 antibody for detecting, managing, monitoring, imaging, diagnosis of various cancers, as well as for drug development.

It is well-known that the LAAO-similar portion conserves key domains and residues that bind the flavin adenine dinucleotide (FAD) cofactor and is required for its enzymatic activity, as well as residues in the active site of the LAAO crystal structure.

Naturally, though specific to a peptide of SEQ ID NO: 2, it is well-known that antibodies can bind peptides with almost same sequence or structural features. Accordingly, antibodies of the invention are also able to bind peptides showing sufficient similarities with SEQ ID NO: 2. Also, the invention relates to antibodies that bind a peptide having similarities with the human IL4I1 sequence REEHIEGGHSNTDRPSR (SEQ ID NO: 2), such as the corresponding mouse IL4I1 sequence which differs of one amino acid in the first position HEEHIEGGHSNTDRPSR (SEQ ID NO: 17) but have conserved the same antigen specificity.

Accordingly, the invention also provides an antibody that binds a peptide having at least 80%, at least 85%, at least 90%, at least 95%, at least 96%, at least 97%, at least 98% or at least 99% identity with sequence set forth as SEQ ID NO:2. More preferably, a peptide having at least 90%, at least 95%, at least 96%, at least 97%, at least 98% or at least 99% identity with sequence set forth as SEQ ID NO:2.

Accordingly, the invention also provides an antibody that binds a peptide having at least 80%, at least 85%, at least 90%, at least 95%, at least 96%, at least 97%, at least 98% or at least 99% identity with sequence set forth as SEQ ID NO:17. More preferably, a peptide having at least 90%, at least 95%, at least 96%, at least 97%, at least 98% or at least 99% identity with sequence set forth as SEQ ID NO:17.

TABLE 3

| Sequence of immunogenic peptide. | |
| --- | --- |
| Human immunogenic peptide | REEHIEGGHSNTDRPSR (SEQ ID NO: 2) |
| Mouse immunogenic peptide | HEEHIEGGHSNTDRPSR (SEQ ID NO: 17) |

Contrary to the teachings of the previous art, the inventors have raised a rabbit monoclonal anti-IL4I1 antibody not binding in the FAD Region. The inventors have cloned and characterized the variable domain of both the light and heavy chains, and thus determined the complementary determining regions (CDRs) domains of said antibody as described in Table 1 and Table 2 below.

TABLE 4

| Protein sequence coding the variable domain of the light and heavy chain (VL and VH) of clone D-5. | |
| --- | --- |
| anti-IL4I1 antibody D-5 IgG/λ: Domains | Protein Sequence |
| VL | ELVLTQSPSVSAALGASAKLTCTLSSAHSTYTIEWYQQQPGESPRYLMQLKSDGS YTKGTGVPDRFSGSSSGADRYLIIFSVQADDEADYYCGANYSSGYVFGGGTQLTV T (SEQ ID NO: 3) |
| L CDR1 | SAHSTYT (SEQ ID NO: 5) |
| L CDR2 | LKSDGSY (SEQ ID NO: 6) |
| L CDR3 | GANYSSGYV (SEQ ID NO: 7) |
| VH | QQQLVESGGDLVKPEGSLTLTCTASGFSLSAGYFICWIRQAPGKGLEWIGSVFSG SSGTTYYASWAKGRFTISKTSSTTVTLQMTSLTAADTAIYFCARGGVLGGRVAYD NSFDHWGPGTLVTVSS (SEQ ID NO: 4) |
| H CDR1 | GFSLSAGYF (SEQ ID NO: 8) |
| H CDR2 | VFSGSSGTT (SEQ ID NO: 9) |
| H CDR3 | ARGGVLGGRVAYDNSFDH (SEQ ID NO: 10) |

TABLE 5

| Nucleotide sequence coding the variable domain of the light and heavy chain (VL and VH) of clone D-5. | |
| --- | --- |
| anti-IL4I1 antibody D-5 IgG/λ: Domains | Nucleotide Sequence |
| VL | GAGCTCGTGCTGACTCAGTCGCCCTCTGTGTCTGCCGCCCTGGGAGCCTCTGCC AAGCTCACCTGCACCCTGAGCAGTGCCCACAGCACCTACACCATTGAATGGTA |

TABLE 5-continued

Nucleotide sequence coding the variable domain of the light and heavy chain (VL and VH) of clone D-5.

anti-IL4I1
antibody D-5
IgG/λ: Domains Nucleotide Sequence

| | |
|---|---|
| | TCAGCAGCAGCCAGGGGAGTCCCCTCGGTACCTGATGCAGCTTAAGAGTGAT<br>GGAAGCTACACTAAGGGGACCGGGGTCCCTGATCGCTTCTGGGCTCCAGCTC<br>TGGGGCTGACCGCTACTTGATCATCTTCAGCGTCCAGGCTGATGACGAAGCCG<br>ACTACTATTGTGGTGCAAATTATAGTAGTGGATATGTGTTCGGCGGAGGGACC<br>CAGCTGACCGTCACA (SEQ ID NO: 11) |
| VH | CAGCAGCAGCTGGTGGAGTCCGGGGGAGACCTGGTCAAGCCTGAGGGATCCC<br>TGACACTCACCTGCACAGCCTCTGGATTCTCCTTAAGTGCCGGCTACTTCATAT<br>GCTGGATCCGCCAGGCTCCAGGGAAGGGGCTGGAGTGGATCCGTTTT<br>TAGTGGGAGTAGTGGTACCACTTACTACGCGAGCTGGGCGAAAGGCCGATTC<br>ACCATCTCCAAAACCTCGTCGACCACGGTGACTCTGCAAATGACCAGTCTGACA<br>GCCGCGGACACGGCCATCTATTTCTGTGCGAGGGGGGGTGTTCTTGGTGGTC<br>GTGTTGCATATGACAACTCTTTTGATCACTGGGGCCCAGGCACCCTGGTCACC<br>GTCTCCTCA (SEQ ID NO: 12) |

TABLE 6

Protein sequence coding the variable domain of the light and heavy chain (VL and VH) of clone A-3.

anti-IL4I1
antibody A-3
IgG/λ: Domains Protein Sequence

| | |
|---|---|
| VL | ELVLTQSPSVSAALGASAKLTCTLSSAHSTYTIDWYQQQPGESPRYLMQLKSDGT<br>YTKGTGVPDRFSGSSSGADRYLIIPSVQADDEAGYYCGANYSGGYVFGGGTQLT<br>VTRTVA (SEQ ID NO: 13) |
| VH | QSLEESGGDLVKPEGSLTLTCTASGFSLSAGYFMCWVRQAPGKGLEWIGSIFSGS<br>SGSTYYASWAKGRFTISKTSSTTVTLQMTSLTAADTAIYFCARGGVVDGRVAYD<br>NSFDHWGPGTLVTVSS (SEQ ID NO: 21) |
| L CDR1 | SAHSTYT (SEQ ID NO: 5) |
| L CDR2 | LKSDGTY (SEQ ID NO: 14) |
| L CDR3 | GANYSGGYV (SEQ ID NO: 15) |
| H CDR1 | GFSLSAGYF (SEQ ID NO: 8) |
| H CDR2 | IFSGSSGST (SEQ ID NO: 18) |
| H CDR3 | ARGGVVDGRVAYDNSFDH (SEQ ID NO: 19) |

TABLE 7

Nucleotide sequence coding the variable domain of the light and heavy chain (VL and VH) of clone A-3.

anti-IL4I1
antibody A-3
IgG/λ: Domains Nucleotide Sequence

| | |
|---|---|
| VL | GAGCTCGTGCTGACTCAGTCGCCCTCTGTGTCTGCCGCCCTGGGAGCCTCTGCC<br>AAGCTCACCTGCACCCTGAGCAGTGCCCACAGCACCTACACCATTGACTGGTA<br>TCAGCAGCAGCCAGGGGAGTCCCCTCGGTACCTGATGCAGCTTAAGAGTGAT<br>GGAACTTACACCAAGGGGACCGGGGTCCCTGATCGCTTCTCGGGCTCCAGCTC<br>CGGGGCTGACCGCTACTTGATCATCCCCAGCGTCCAGGCTGATGACGAAGCCG<br>GCTACTATTGTGGTGCAAATTATAGCGGTGGGTATGTGTTCGGCGGAGGGAC<br>CCAGCTGACCGTCACACGAACTGTGGCT (SEQ ID NO: 16) |
| VH | CAGTCGTTGGAGGAGTCCGGGGGAGACCTGGTCAAGCCTGAGGGATCCCTGA<br>CACTCACCTGCACAGCCTCTGGATTCTCCTTAAGTGCCGGCTACTTCATGTGCT |

TABLE 7-continued

Nucleotide sequence coding the variable domain of the light and heavy chain (VL and VH) of clone A-3.

anti-IL4I1
antibody A-3
IgG/λ: Domains Nucleotide Sequence

```
GGGTCCGCCAGGCTCCAGGGAAGGGGCTGGAGTGGATCGGATCCATTTTTAG
TGGTAGTAGTGGTAGTACTTACTACGCGAGCTGGGCGAAAGGCCGATTCACC
ATCTCCAAAACCTCGTCGACCACGGTGACTCTGCAAATGACCAGTCTGACAGC
CGCGGACACGGCCATCTATTTCTGTGCGAGGGGGGGTGTTGTTGATGGTCGT
GTTGCATATGACAACTCTTTTGATCACTGGGGCCCAGGCACCCTGGTCACCGTC
TCCTCA (SEQ ID NO: 20)
```

Therefore, the invention relates to a monoclonal antibody having specificity for IL4I1 comprising a light chain wherein the variable domain comprises at least one CDR having a sequence selected from the group consisting of SEQ ID NO:5 for L-CDR1, SEQ ID NO:6 or SEQ ID NO:14 for L-CDR2 and SEQ ID NO:7 or SEQ ID NO:15 for L-CDR3.

The invention also relates to a monoclonal antibody having specificity for IL4I1 comprising a heavy chain wherein the variable domain comprises at least one CDR having a sequence selected from the group consisting of SEQ ID NO:8 for H-CDR1, SEQ ID NO:9 or SEQ ID NO: 18 for H-CDR2 and SEQ ID NO:10 or SEQ ID NO: 19 for H-CDR3.

The monoclonal antibody of the invention, may comprise a light chain wherein the variable domain comprises at least one CDR having a sequence selected from the group consisting of SEQ ID NO:5 for L-CDR1, SEQ ID NO:6 or SEQ ID NO:14 for L-CDR2 and SEQ ID NO:7 or SEQ ID NO:15 for L-CDR3 and a heavy chain wherein the variable domain comprises at least one CDR having a sequence selected from the group consisting of SEQ ID NO:8 for H-CDR1, SEQ ID NO:9 or SEQ ID NO: 18 for H-CDR2 and SEQ ID NO:10 or SEQ ID NO: 19 for H-CDR3.

In particular, the invention provides an anti-IL4I1 monoclonal antibody comprising:
a heavy chain variable region comprising SEQ ID NO:8 in the H-CDR1 region, SEQ ID NO:9 in the H-CDR2 region and SEQ ID NO:10 in the H-CDR3 region; and
a light chain variable region comprising SEQ ID NO:5 in the L-CDR1 region, SEQ ID NO:6 in the L-CDR2 region and SEQ ID NO:7 in the L-CDR3 region.

In particular, the invention provides an anti-IL4I1 monoclonal antibody comprising:
a heavy chain variable region comprising SEQ ID NO:8 in the H-CDR1 region, SEQ ID NO:18 in the H-CDR2 region and SEQ ID NO:19 in the H-CDR3 region; and
a light chain variable region comprising SEQ ID NO:5 in the L-CDR1 region, SEQ ID NO:14 in the L-CDR2 region and SEQ ID NO:15 in the L-CDR3 region.

In a particular embodiment, the heavy chain variable region (VH) of said antibody has the amino acid sequence set forth as SEQ ID NO:4 and/or the light chain variable region (VL) has the amino acid sequence set forth as SEQ ID NO:3 or SEQ ID NO: 13.

In another particular embodiment, the heavy chain variable region (VH) of said antibody has the amino acid sequence set forth as SEQ ID NO:21 and/or the light chain variable region (VL) has the amino acid sequence set forth as SEQ ID NO:3 or SEQ ID NO:13.

In a more particular embodiment, the heavy chain variable region (VH) of said antibody has the amino acid sequence set forth as SEQ ID NO:4 and the light chain variable region (VL) has the amino acid sequence set forth as SEQ ID NO:3.

In a more particular embodiment, the heavy chain variable region (VH) of said antibody has the amino acid sequence set forth as SEQ ID NO:13 and the light chain variable region (VL) has the amino acid sequence set forth as SEQ ID NO:21.

In another embodiment, the monoclonal antibody of the invention is a chimeric antibody, preferably a chimeric rabbit/human antibody. In particular, said rabbit/human chimeric antibody may comprise the variable domains of anti-IL4I1 antibody as defined above.

In another embodiment, the monoclonal of the invention is a humanized antibody. In particular, in said humanized antibody, the variable domain comprises human acceptor frameworks regions, and optionally human constant domain where present, and non-human donor CDRs, such as rabbit CDRs as defined above.

In another aspect, the invention relates to a polypeptide with the same binding specificity toward IL4I1 than antibodies of the invention, and which comprises a sequence selected from the group consisting of SEQ ID NO: 3, SEQ ID NO:4, SEQ ID NO:5, SEQ ID NO:6, SEQ ID NO:7, SEQ ID NO: 8, SEQ ID NO:9, SEQ ID NO:10, SEQ ID NO:13, SEQ ID NO:14, SEQ ID NO:15, SEQ ID NO:21, SEQ ID NO:18 or SEQ ID NO:19.

In another aspect the invention relates to a nucleic acid sequence comprising a sequence selected from the group consisting of SEQ ID NO:11, SEQ ID NO:12, SEQ ID NO:16 and/or SEQ ID NO:20. In a more particular aspect, the invention relates to an hybridoma comprising a nucleic acid sequence comprising a sequence selected from the group consisting of SEQ ID NO:11, SEQ ID NO:12, SEQ ID NO:16 and/or SEQ ID NO:20. In an even more particular embodiment, the invention relates to an hybridoma comprising a nucleic acid sequence comprising a sequence selected from the group consisting of SEQ ID NO:11 and SEQ ID NO:12 or SEQ ID NO:16 and SEQ ID NO:20.

In a further aspect, the invention relates to an hybridoma comprising a nucleotide sequence encoding antibodies, said hybridoma comprising at least one amino acid sequence coding for a polypeptide of a sequence selected from SEQ ID NO: 3, SEQ ID NO:4, SEQ ID NO:5, SEQ ID NO:6, SEQ ID NO:7; SEQ ID NO: 8; SEQ ID NO:9, SEQ ID NO:10, SEQ ID NO:13, SEQ ID NO:14, SEQ ID NO:15, SEQ ID NO:21, SEQ ID NO:18 and SEQ ID NO:19 or a combination thereof, as disclosed above. In a particular embodiment, said hybridoma comprises at least one nucleotide sequence coding for peptide of SEQ ID NO:13 and for a peptide of SEQ ID NO:21. In another particular embodiment, said hybridoma comprises at least one nucleotide sequence coding for a peptide of SEQ ID NO:3 and for a peptide of SEQ ID NO:4. In another particular embodiment, said hybridoma comprises at least a nucleotide sequence coding for peptides SEQ ID NO:5, SEQ ID NO:6, SEQ ID NO:7, SEQ ID NO: 8, SEQ ID NO:9, and SEQ ID NO:10. In another particular embodiment, said hybridoma comprises at least a nucleotide sequence coding for peptides SEQ ID NO:5, SEQ ID NO:14, SEQ ID NO:15, SEQ ID NO: 8, SEQ ID NO:18, and SEQ ID NO:19.

Methods for Producing Antibodies of the Invention.

An object of the invention relates to a hybridoma cell producing an antibody according to the invention. Briefly, hybridoma cell may be produced according to conventional methods, including immunization of an animal and spleen cells to produce hybridomas by fusion with PEC between spleen cells and appropriate cell lines. Appropriate cell lines are well-known in the art.

Alternately, fragment or derivative of antibodies of the present invention may be produced by any technique known in the art, such as, recombinant processes.

In particular the inventors have deposited a rabbit anti-human-IL4I1 antibody (D-5)-producing hybridoma cell at the Collection Nationale de Cultures de Microorganismes (CNCM, Institut Pasteur, 25 rue du Docteur Roux, 75724 Paris Cedex 15, France), in accordance with the terms of Budapest Treaty, on Sep. 26, 2018. The deposited hybridoma has CNCM deposit number I-5355.

Further, anti-IL4I1 antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternately, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

As exposed in the experimental data, the antibodies of the invention have been isolated from hybridoma obtained from animals immunized by peptide of sequence SEQ ID NO:2. Thus, the invention also relates to a method for producing an antibody comprising the use of a peptide having a sequence selected from SEQ ID NO:2 (REEHIEGGHSNTDRPSR).

Accordingly, a further object of the invention relates to a nucleic acid sequence encoding an antibody according to the invention. More particularly the nucleic acid sequence encodes a heavy chain or a light chain of an antibody of the invention. Even more particularly, the nucleic acid sequence encoding a heavy chain comprises SEQ ID NO:12 or SEQ ID NO:20 and the nucleic acid sequence encoding a light chain comprises SEQ ID NO:11 or SEQ ID NO:16.

Typically, said nucleic acid is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention. Such vectors may comprise regulatory elements, such as a promoter, enhancer, terminator and the like, to cause or direct expression of said antibody upon administration to a subject.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSGI beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc.

Protocols for producing such replication-defective recombinant viruses are techniques commonly known in the art.

A further object of the present invention relates to a host cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors.

Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.).

The present invention also relates to a method of producing a recombinant host cell expressing an antibody according to the invention, said method comprising the steps of:
  (i) introducing in vitro or ex vivo a recombinant nucleic acid or a vector as described above into a competent host cell,
  (ii) culturing in vitro or ex vivo the recombinant host cell obtained and
  (iii) optionally, selecting the cells which express and/or secrete said antibody. Such recombinant host cells can be used for the production of antibodies of the invention.

In another particular embodiment, the method comprises the steps of:

(i) culturing the hybridomas according to the invention under conditions suitable to allow expression of antibody of the invention; and (ii) recovering the expressed antibody.

Antibodies of the invention are suitably separated from the culture medium by conventional immunoglobulin purification procedures such as, for example, protein ASepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well-known in the art.

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred.

Methods for producing humanized antibodies based on conventional recombinant DNA and gene transfection techniques are well-known in the art. Antibodies can be humanized using a variety of techniques known in the art including, for example, CDR-grafting, veneering or resurfacing, and chain shuffling. The general recombinant DNA technology for preparation of such antibodies is also known.

The Fab of the present invention can be obtained by treating an antibody which specifically reacts with IL4I1 with a protease, papain. Also, the Fab can be produced by inserting DNA encoding Fab of the antibody into a vector for prokaryotic expression system, or for eukaryotic expression system, and introducing the vector into a prokaryote or eukaryote (as appropriate) to express the Fab.

The F(ab')2 of the present invention can be obtained treating an antibody which specifically reacts with IL4I1 with a protease, pepsin. Also, the F(ab')2 can be produced by binding Fab' described below via a thioether bond or a disulfide bond.

The Fab' of the present invention can be obtained treating F(ab')2 which specifically reacts with IL4I1 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well-known technology called CDR grafting may be used, which involves selecting the complementary determining regions (CDRs) from a donor scFv fragment, and grafting them onto a human scFv fragment framework of known three dimensional structure.

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a nonhuman animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2);

glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method. A "function-conservative variant" also includes a polypeptide which has at least 60% amino acid identity as determined by BLAST or FASTA algorithms, preferably at least 75%, more preferably at least 80%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wisconsin) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein. As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well-known to those of skill in the art and include: arginine and lysine; glutamate and aspartate; serine and threonine; glutamine and asparagine; and valine, leucine and isoleucine.

Accordingly, the invention also provides an antibody comprising a heavy and light chain wherein the variable domain comprises:
   a H-CDR1 having at least 80% or 85% identity with sequence set forth as SEQ ID NO:8,
   a H-CDR2 having at least 80% or 85% identity with sequence set forth as SEQ ID NO:9 or SEQ ID NO:18,
   a H-CDR3 having at least 80% or 85% identity with sequence set forth as SEQ ID NO:10 or SEQ ID NO:19,
   a L-CDR1 having at least 80% or 85% identity with sequence set forth as SEQ ID NO: 5,
   a L-CDR2 having at least 80% or 85% identity with sequence set forth as SEQ ID NO:6 or SEQ ID NO:14,
   a L-CDR3 having at least 80% or 85% identity with sequence set forth as SEQ ID NO:7 or SEQ ID NO:15, and
   that specifically binds to SEQ ID NO: 2 with substantially the same affinity as an antibody comprising a heavy chain wherein the variable domain comprises SEQ ID NO:8 for H-CDR1, SEQ ID NO:9 or SEQ ID NO:18 for H-CDR2 and SEQ ID NO: 10 or SEQ ID NO:19 for H-CDR3 and a light chain wherein the variable domain comprises SEQ ID NO: 5 for L-CDR1, SEQ ID NO: 6 or SEQ ID NO:14 for L-CDR2 and SEQ ID NO: 7 or SEQ ID NO:15 for L-CDR3, and more preferably with substantially the same affinity as the anti-IL4I1 antibody with a VL domain of SEQ ID NO: 3 or SEQ ID NO:13 and/or a VH domain of SEQ ID NO: 4 or SEQ ID NO: 21.

More particularly, the invention also provides an antibody comprising a heavy and light chain wherein the variable domain comprises:
   a H-CDR1 having at least 90% or 95% identity with sequence set forth as SEQ ID NO:8,
   a H-CDR2 having at least 90% or 95% identity with sequence set forth as SEQ ID NO:9 or SEQ ID NO:18,
   a H-CDR3 having at least 90% or 95% identity with sequence set forth as SEQ ID NO:10 or SEQ ID NO:19,
   a L-CDR1 having at least 90% or 95% identity with sequence set forth as SEQ ID NO: 5,
   a L-CDR2 having at least 90% or 95% identity with sequence set forth as SEQ ID NO:6 or SEQ ID NO:14,
   a L-CDR3 having at least 90% or 95% identity with sequence set forth as SEQ ID NO:7 or SEQ ID NO:15, and
   that specifically binds to SEQ ID NO: 2 with substantially the same affinity as an antibody comprising a heavy chain wherein the variable domain comprises SEQ ID NO:8 for HCDR1, SEQ ID NO:9 or SEQ ID NO:18 for H-CDR2 and SEQ ID NO: 10 or SEQ ID NO:19 for H-CDR3 and a light chain wherein the variable domain comprises SEQ ID NO: 5 for L-CDR1, SEQ ID NO: 6 or SEQ ID NO:14 for L-CDR2 and SEQ ID NO: 7 or SEQ ID NO:15 for L-CDR3, and more preferably with substantially the same affinity as the anti-IL4I1 antibody with a VL domain of SEQ ID NO: 3 or SEQ ID NO:13 and/or a VH domain of SEQ ID NO: 4 or SEQ ID NO: 21.

Accordingly, the invention also provides an antibody which binds to IL4I1, in particular to the epitope of SEQ ID NO:2. The invention more particularly provides an antibody which binds specifically to the epitope of SEQ ID NO:2.

Said antibodies may be assayed for specific binding by any method known in the art. Many different competitive binding assays can be used for epitope binning. The immunoassays which can be used include, but are not limited to, competitive assay systems using techniques such western blots, radio-immunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well-known in the art.

Device and Kit.

In another embodiment, the invention relates to a device comprising at least one antibody according to the invention immobilized on a support.

In a preferred embodiment, the support is a membrane, a slide, a microarray, a chip, a microbead or a quartz prism.

A further object of the invention is a kit comprising a device as defined above and a reagent to perform or detect an immune reaction, particularly an antibody-antigen complex. The kits typically comprise containers for the different reagents and products and may further comprise a support or other device suitable to perform the assay.

The antibodies can be used individually or in combination to measure the level of IL4I1, using any number of detection technologies or platforms such as, without limitation Capture assay, Sandwich assay, Competition assay, Radio-immuno assays, Enzyme labels with substrates that generate colored, fluorescent, chemiluminescent, or electrochemically-active products, Fluorescence, fluorescent polarization, Chemiluminescence, Optical and colorimetric, Electrochemiluminescence, Time-resolved fluorescence, Surface plasmon resonance, Evanescent wave, Multiwell plate (ELISA), Individual assay, Multiplex assay, Latex bead-multiplex assay, Microarray (Laminar surface)-multiplex assay, Glass, Ceramic (like RANDOX ceramic), Plate based assays, Strip based assays, dipsticks, Closed systems immunoassays. Preferred assay formats include:

Capture Assay.

An assay carried out using a single immobilized antibody (multiwall plate, latex bead, microarray, etc.) which captures a specific labeled protein from a biofluid, the detection which is measured using appropriate detection reagents as detailed in the following paragraph.

The antibody is immobilized directly to the support or captured by an affinity reagent such as an anti-mouse IgG antibody coated onto the support. The immobilized antibody is then incubated with any of the above-mentioned body fluids in which the proteins have been labeled with a detection molecule such as biotin, with or without pre-treatment to remove abundant proteins. The labeled protein which is bound by the antibody is detected by the addition of an appropriate detection reagent which binds to the label such as avidin or streptavidin which has been modified to be compatible with one of the detection technologies described in the section "detection technology."

The resulting signal provides a quantitative measure of the amount of labeled protein bound by the antibody.

Sandwich ELISA.

An assay using two antibodies, the first which is immobilized on a support (multiwell plate, latex bead, microarray, etc.) which binds a specific protein from a biofluid, the detection which is measured using a labeled second antibody against the same protein and appropriate detection reagents as detailed in the following paragraph.

The first antibody is immobilized directly to the support or captured by an affinity reagent such as an anti-mouse IgG antibody coated onto the support. The immobilized antibody is then incubated with any of the above-mentioned body fluids, with or without pre-treatment to remove abundant proteins. The antibody/antigen complex is then incubated with a second antibody, made against the same protein, which has been labeled with a detection molecule such as biotin. The bound antibody is detected by the addition of an appropriate detection reagent which binds to the label such as avidin or streptavidin which has been modified to be compatible with one of the detection technologies described in the section "detection technology." The resulting signal provides a quantitative measure of the amount of protein bound by the antibody Competitive Assay.

An assay in which the binding of a labeled tracer protein by a single antibody as described in "capture assay" is inhibited by pre-incubation of a biofluid to indirectly quantify the analyte.

The antibody is immobilized directly to the support or captured by an affinity reagent such as an anti-mouse IgG antibody coated onto the support. The immobilized antibody is then incubated with any of the above-mentioned body fluids. The immobilized antibody/antigen complex is then incubated with a labeled tracer consisting of either (1) any of the above mentioned body fluids in which the proteins have been labeled with a detection molecule such as biotin, with or without pre-treatment to remove abundant proteins, or (2) a purified or recombinant protein recognized (bound) by the monoclonal antibody, or (3) a peptide which is recognized (bound) by the monoclonal antibody. The labeled protein or peptide which is bound by the antibody is detected by the addition of an appropriate detection reagent which binds to the label such as avidin or streptavidin which has been modified to be compatible with one of the detection technologies described in the section "detection technology."

The level of the specific protein in the unlabeled biofluid is determined as a function of the inhibition of signal.

Preferred Detection Technologies include:

Enzyme labels with substrates that generate colored, fluorescent, chemiluminescent, or electrochemically-active products.

The detection reagent (for example steptavidin or avidin, which binds to biotin) is coupled to an enzyme such as horseradish peroxidase which is capable of catalyzing:

an appropriate colorimetric substrate of which the product demonstrates maximal absorbance at a given wavelength allowing the quantitative measurement of the labeled protein by measuring the optical density of the final product in the well at or near the wavelength of maximal absorbance.
  a chemiluminescent substrate to a sensitized reagent which upon oxidation emits light, providing the quantitative measurement of the labeled protein.
  a chemiluminescent substrate to a sensitized reagent which upon the application of an electrical current emits light, providing the quantitative measurement of the labeled protein.

Fluorescence.

The detection reagent (for example streptavidin or avidin, which binds to biotin) is coupled to a fluorescent tag.

Preferred platform Technologies include:

Multiwell Plate.

Single test: one antibody is immobilized per well either directly or indirectly using a capture reagent such as goat anti-mouse antibody.
  Multiplex: 2 or more antibodies are immobilized in a single well by deposition in a pattern Latex Bead.

Two or more antibodies are immobilized onto a latex bead between x and y microns Arrays, Microarrays, and Nanoarrays.

Two or more antibodies are spotted onto an activated laminar surface with a spot diameter between 100 µm-5 mm (arrays), 2 µm-100 µm (microarrays), 10 nm-2 am (nanoarrays) The surface can be composed of glass, plastic, ceramic, carbon nanotube lattice etc.

Prism Quartz.

A biocaptor can be constructed using the antibody immobilized on gold nanoparticles. The nanoparticles are deposited on a quartz surface. The vibration frequency of the quartz submitted to electric current is modified by the presence of the nanoparticles. The specific ligation of the IL4I1 protein to the antibody slows down the vibration frequency in proportion to the weight of the bound protein.

A further object of the invention is thus a kit comprising an anti-IL4I1 antibody according to the invention or a device as mentioned above, suitable to be used for detecting the level or presence of IL4I1.

A further object of the invention is thus a kit comprising an anti-IL4I1 antibody according to the invention or a device as mentioned above, suitable to be used for detecting the level or presence of IL4I1. In a particular embodiment, said kit further comprises at least one reagent for performing or detecting an immune reaction, particularly an antibody-antigen complex Detection Uses.

The second aspect of the invention relates to an anti-IL4I1 antibody for detecting, managing, monitoring, imaging, diagnosis a cancer disease, especially cancer with IL4I1-expressing cells.

In a particular embodiment, the invention relates to an anti-IL4I1 antibody as described above for detecting, managing, monitoring, imaging, diagnosis a cancer disease, especially cancer with IL4I1-expressing cells.

In a preferred embodiment, antibodies of the invention are particularly suited for use detecting, managing, monitoring, imaging, diagnosis cancer diseases associated with IL4I1-expressing cells including, but not limited to, B-cell lymphoid malignancies, such as follicular lymphoma, Hodgkin lymphoma, primary mediastinal B cell lymphoma, diffuse large B cell lymphoma, marginal zone lymphoma and chronic lymphoid leukemia, ovarian carcinomas, mesotheliomas, colon carcinomas, breast carcinomas, melanomas, glioblastomas and lung carcinomas, preferably displaying IL4I1-expressing cells or any cancer intended to be treated by an immune checkpoint inhibitor (anti-PD-1 or anti-PD-L1 or anti CTLA4). More specifically, such cancer intended to be treated by an immune checkpoint inhibitor is a cancer wherein at least some of the tumor cells—or immune cells that have infiltrated the tumor—express the target of the immune check inhibitor, PD1, PDL1 or CTLA4.

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with IL4I1 overexpression, and in a preferred embodiment from B-cell lymphoid malignancies, such as follicular lymphoma, Hodgkin lymphoma, primary mediastinal B cell lymphoma, diffuse large B cell lymphoma, marginal zone lymphoma and chronic lymphoid leukemia, ovarian carcinomas, mesotheliomas, colon carcinomas, breast carcinomas, melanomas, glioblastomas and lung carcinomas. Therefore, biological samples encompass clinical samples, cells in culture, primary cell suspensions, cell supernatants, cell lysates, serum, plasma, biological fluid, and tissue samples.

In another embodiment of the invention, antibodies of the invention are used in histopathological classification or immunostaining of cancers in vitro or ex vivo for detecting, diagnosing, monitoring, managing or imaging cancer with IL4I1-expressing cells.

In a particular embodiment, the invention provides a method for detecting or diagnosing a cancer in a subject, wherein the cancer to be treated displays IL4I1-expressing cells and the subject displays an IL4I1-positive status, the method comprising:
  contacting a sample from said subject with an antibody of the present invention, and
  determining the presence of an antigen bound to said antibody, said presence being indicative of IL4I1-positive status in said subject.

In order to monitor the cancer disease, the method of diagnosing according to the invention may be repeated at different intervals of time, in order to determine if antibody binding to the samples increases or decreases, whereby it is determined if the cancer disease progresses or regresses.

In another embodiment, the invention provides a method for determining the chances of a patient suffering from IL4I1-positive cancer to respond to a treatment comprising the administration of an IL4I1 inhibitor, comprising the following step:
  a. using an antibody according to the present invention to determine the presence or level of IL4I1 from a biological sample of said patient;
  b. comparing IL4I1 presence obtained in step a) with a reference value; said presence or level being indicative of IL4I1-positive status; and
  c. determining patients responding to treatment comprising the administration of an inhibitor of IL4I1.

The presence of IL4I1 from a biological sample is determined by techniques which are well-known in the art such as immunohistochemistry, immunohistology, flow cytometry, ELISA and other immunodetection techniques.

As used herein, the "reference sample" or "reference value" which is used to detect an overexpression of IL4I1 is a biological sample from a subject that does not suffer from cancer with IL4I1-expressing cells. Preferably, it is a biological sample of a healthy subject that has neither antecedent of nor predisposition to cancer with IL4I1-expressing cells. More preferably, it is a biological sample obtained from a subject who has undergone a biopsy revealing that it does not suffer from cancer with IL4I1-expressing cells. More preferably, it is a biological sample obtained from a healthy subject. Alternately, it is a healthy biological sample obtained from a subject suffering from cancer with IL4I1-expressing cells, for example the healthy biological sample is healthy tissue adjacent to the tumor. Determining the presence of IL4I1 of the invention in said reference sample enables to set a "reference value" (for quantitative measurements) or "reference status" (for qualitative measurements) that are then compared with the actual expression value (amount) or status (level) of the tested subject. It is possible to use, as "reference amount" or "reference level" in the methods of the invention, an average expression amount or level of the same protein which has been measured in several reference samples.

In a particular embodiment, the method for determining the chances of a patient suffering from IL4I1-positive cancer to respond to a treatment comprises the administration of an IL4I1 inhibitor and the presence of IL4I1 is determined by immunohistochemistry, flow cytometry, mass cytometry (CyTOF) and/or soluble immunodetection such as ELISA.

In another embodiment, the method for determining the chances of a patient suffering from IL4I1-positive cancer to respond to a treatment comprising the administration of an IL4I1 inhibitor, wherein the method comprising:
a. measuring IL4I1 expression level from a biological sample of said patient;
b. comparing IL4I1 expression level obtained in step a. with a reference value; and
c. determining patients responding to treatment comprising the administration of an inhibitor of IL4I1.

Alternately, the method for determining the chances of a patient suffering from an IL4I1-positive cancer, to respond to a treatment comprising the administration of an IL4I1 inhibitor, said method comprising the following steps:
a. using an antibody according to the present invention to determine the presence or level of IL4I1 from a biological sample of said patient;
b. comparing said IL4I1 presence or level obtained in step a. with a reference value; said presence or level being indicative of IL4I1 positive status; and
c. determining from step b. whether said patient has chances to respond to treatment comprising the administration of an inhibitor of IL4I1.

In each of these embodiments related to the method for determining the chances of a patient suffering from IL4I1-positive cancer to respond to a treatment, said treatment comprising the administration of an IL4I1 inhibitor, the step a. is performed using an antibody according to the invention antibodies which binds specifically to the region of the 365-381 amino acid sequence of IL4I1 (SEQ ID NO: 2) as disclosed above.

In another embodiment the invention also relates to a method of treating a patient suffering from an IL4I1-positive cancer, said method comprising the steps of:
a. using an antibody according to claim 1 to determine the presence or level of IL4I1 from a biological sample of said patient;
b. comparing IL4I1 presence or level obtained in step a. with a reference value; said presence or level being indicative of IL4I1 positive status;
c. determining from step b. whether said patient has chances to respond to treatment comprising the administration of an inhibitor of IL4I1; and
d. administering to said patient an inhibitor of IL4I1 and/or an immune checkpoint inhibitor.

Such inhibitors are known from the skilled in the art, and are notably listed in WO2010/066858, the contents of which are hereby incorporated by reference.

Immune checkpoint inhibitors are also well-known from the skilled in the art and are for example CTLA4 inhibitors, PDL1 inhibitors or PD1 inhibitors. A non-limitative list of such inhibitors comprises for example ipilimumab, nivolumab, pembrolizumab, atezolizumab, avelumab, durvalumab, cemiplimab or pidilizumab.

Further aspects and advantages of the invention will be disclosed in the following examples, which should be considered illustrative.

EXAMPLE

Example 1. Method of Production

Hybridoma Production.

IL4I1 hybridoma of the invention may be produced by any technique known in the art, particularly by methods disclosed in U.S. Pat. Nos. 5,675,063 and 7,429,487 incorporated by reference herein. Briefly, monoclonal antibodies against IL4I1 were developed by sequential immunization (5 injections) of three rabbits. Rabbits were hyperimmunized with KLH conjugates of immunogens peptides (SEQ ID NO: 2).

Peptide-protein conjugates are used to induce the production of antibodies against peptides. Peptide-protein conjugates of the invention may be produced by any technique known in the art. According to the invention, peptide-protein conjugates are KLH conjugates.

Peptides alone are generally too small to elicit a sufficient immune response, carrier proteins that contain several epitopes are used to stimulate T-helper cells, which subsequently facilitate the induction of the B-cell response. Multiple antigenic peptides (MAPs) are an alternative approach that can be used to raise anti-peptide antibodies. This approach has several advantages over the traditional methodologies including eliminating the conjugation step, which can be time consuming and also result in random product mixtures.

The immune system reacts to the entire peptide-protein conjugate; therefore, some antibodies will always be raised against the peptide, the linker, and the carrier protein. As such, it is important to use a conjugate during immunization that differs from any that might be used in the final assays. For example, without limiting the scope of the invention, KLH conjugates should be used to immunize for antibodies when BSA conjugates are used in the end-point assays. The most commonly used carrier proteins are as follows:

KLH (keyhole limpet hemocyanin) is a copper-containing protein that is found in arthropods and mollusca. Therefore, it is an ideal carrier to use in mammalian hosts such as rabbits and mice. It is isolated from *Megathura crenulata* and has a MW that ranges from $4.5 \times 10^5$ to $1.3 \times 10^7$ Da. KLH is the carrier that is used most commonly because it has a higher immunogenicity than does BSA. However, its solubility in water is limited because of its size and structure, which results in a cloudy appearance. The turbidity does not affect immunogenicity, and the resulting solution can be used for successful immunizations.

BSA (bovine serum albumin) is a plasma protein in cattle that is one of the most stable and soluble albumins available. It has a MW of $67 \times 10^3$ Da and includes 59 lysines. Of these, ~30-35 are accessible for use in linker conjugation, and so BSA is a popular carrier protein for weakly antigenic compounds. BSA is more water-soluble that KLH because it is smaller; therefore, it is used more commonly in immunoassays. However, because BSA is commonly used to block nonspecific binding sites in antibody-based assays BSA conjugates should not be used for immunization if the end-point assay system uses BSA. This is because if antisera against peptide-BSA conjugates are used in these assays, false positives are common because the sera used also contain antibodies against BSA.

Conjugation Protocols.

The antigenic peptide used to produce anti-IL4I1 antibodies of the invention, may be produced by any technique known in the art, such as the protocol below.

The antigenic peptide was coupled through a Ahx spacer and a cysteine to KLH for the priming and boosting injections in rabbit. The antigenic peptide coupled to BSA was used for ELISA screening.

Conjugation using cysteine residues.
1. This type of conjugation requires either a N- or C-terminal cysteine.
2. A total of 3 mg m-maleimidobenzoyl-N-hydroxysuccinimide ester (MBS) is dissolved in 200 ul dimethyl formamide (DMF).
3. Next, 70 ul MBS/DMF is added to a KLH solution consisting of 5 mg KLH in 0.5 ml 10 mM phosphate buffer, pH 7.0, and it is stirred gently at room temperature for 30 min.
4. The free crosslinker is removed using a SEPHADEX G25 size exclusion column. First, the column is equilibrated in 50 mM phosphate buffer (pH 6.0). The KLH reaction mixture is then loaded and eluted using 50 mM phosphate buffer (pH 6.0). Collect the 3.5 mL of purified KLH/MBS or BSA/MBS. Add 0.5 mL of water.
5. A total of 5 mg synthetic peptide is dissolved in 100 μL of DMF. Rapidly add 1 mL of purified KLH/MBS or BSA/MBS. Shake rapidly and immediately add 11 μL of 2 N NaOH to adjust the pH between 7.0-7.2. The reaction will stop if the pH is not in the right range.
6. The mixture is stirred for 3 hours at room temperature or overnight at 4° C.
7. Add 3 mL of ammonium bicarbonate (0.1 M) before Lyophilization.

A subcutaneous injection with 0.3 mg of the conjugate was administered to three rabbits on days 0, and boosts were performed with 0.15 mg of conjugate on days 21, 35, 49 and 63.

On day 0, the pre-immune serum from the rabbits was taken and store frozen as a blank when performing ELISA after immunization. Then, rabbits were primed with 300 μg of immunogen.

On day 61, animals were bled and antibody response tested by ELISA to verify the specific antibody production against the peptide of interest.

On day 63, a last boost with the conjugated peptide was realized and two weeks after a final bleed was performed to select the better producing rabbit and splenocytes removed and frozen.

After the selection of the better responding rabbit, its splenocytes were thawed and put in culture.

Subsequently, spleen cells from the selected rabbit were fused with rabbit myeloma 240E-W2 cells (property of Epitomics). Cells were cultured in plates with HAT medium for hybridoma selection. After a minimum of 7 days, the supernatants were harvested and screened for IL4I1 binding specificity by direct enzyme-linked immunosorbent assay (ELISA). Later, positive clones were expanded into 24-well plates and a secondary ELISA screen was performed to confirm the positive clones.

Ninety-one clones (hybridomas) were generated and were expanded into 24-well plates. Forty-three of them were selected on the basis of ELISA values as the best antibody producers and were screened by Western blot against HEK293 cells expressing or not recombinant human IL4I1. Sixteen of these were positive and were further tested by immunohistochemistry on human lymphoid tissues (reactive lymph nodes and human lymphomas).

The two best hybridomas were then chosen to be sub-cloned. Ten sub-clones were initially selected by an ELISA screen against the antigenic peptide and a measure of IgG concentration. Subsequently, they were tested for the recognition of the whole human IL4I1 protein by Western blot and immunohistochemistry. Two sub-clones were then chosen and expanded for large scale in vitro production of anti-IL4I1 antibodies.

Hybridoma Culture.

The hybridoma culture protocol used in the present invention is well-known in the art. For example, hybridoma may be cultivated as below.

Hybridoma Growth Medium (240E media) with 1×HAT; RPM11640, 1000 ml; CELLGRO MEDIUM, cat #: 10-040-CM, RPMI 1640, 1×, with L-glutamine; Rabbit Hybridoma Supplement A (contains Gentamycin Sulfate); 2 vials (40 mls each); 55 μM 2-Mercaptoenthanol cell culture grade 1:1000 (1.24 ml) of 55 mM stock solution (Invitrogen, cat. #21985-023); Fetal Bovine Serum 124 ml; HYCLONE FETAL CLONE I medium, VWR Catalog #16777-232, Thermo Scientific cat #SH30080.03.

You can prepare this medium and store it at 4° C. for a couple of weeks. When taking out of the fridge and opening a new medium bottle please add freshly:
1) 1×HAT (catalog number: MT-25-046-CI) 25 ml of 50× stock solution
2) GLUTAMAX-1 supplement from GIBCO (Invitrogen), Cat #35050-061 (100×, liquid) 12.4 ml (Thaw supplement overnight in refrigerated conditions, 2° C.-8° C. Aseptically add the required volume to culture medium. Store remaining supplement at −5° C. to −20° C. GLUTAMAX supplement can be frozen and thawed repeatedly with no loss of potency.)

Antibodies Production.

The antibodies of the present invention may be produced by any techniques known in the art, such as the protocol below.

Thawing Cells:
1. Take cells from liquid N2, immediately thaw in water bath at 37° C.
2. Transfer cells to a 15 ml tube with 10 ml of warm medium.
3. Spin cells at 240 g for 5 min at room temperature, aspirate supernatant.
4. Resuspend cells in one ml of warm medium.
5. Plate cells into petri-dish (10 cm) with 15 ml media, 1 vial/1 dish or into 1.6-well plate, 1 vial/well depending on how big the cell pellet is.
6. 1-2 days later observe under microscope, aspirate top medium with any floating cells.
7. Split cells at 70-80% confluence.

Hybridoma Maintenance:
1. Hybridoma maintenance is done every 3-4 days on all 24-well plates.
2. Observe under the microscope for growth condition of each hybridoma
(see photos at end of document). Cells are ready to split at 70-80% density
2. (medium color orange/slightly yellowish).
3. Use a 1000 μl pipet and sterile filter tips. Be sure to change tips between each well.
4. Shake the plates gently and let the cells float. For each well, take out approx 80% medium
5. with cells (about 1 ml). Leave 20% in well, add 80% medium back into well.
6. If some wells are growing slower, take only half of the media out.
7. Replenish each well with the same volume of 1×HAT 240E media (about 1 ml).

Serum-Free Medium.

Irvine Scientific IS MAB-CD (Cat #91104) supplemented with 1% antibiotic/antimycotic (from Cellgro company Cat

30-004-CI: add 10 ml for 1 l medium), and 4% GLUTA-MAX supplement (from Gibco Cat. #35050-061: add 40 ml for 1 l medium). DO NOT ADD SUPPLEMENT A.

Antibody Production Method:
1. Expand each hybridoma in growth medium by thawing a frozen vial into a 10 cm Petri dish.
2. Grow the cells in 10 cm Petri dish until 70-80% density.
3. Expand the cells from 10 cm Petri dish to T175 flask until 70-80% density (medium color orange/slightly yellowish) by harvesting the cells as follows: Pellet at 1000 rpm, resuspend in 60 ml hybridoma growth medium.
4. Grow the cells in the T175 flask (Corning catalogue number 431080) until 70-80% density (medium color orange/slightly yellowish). Typical antibody concentration in the supernatant: 1-10 µg/ml.
5. Expand the cells from 1×T175 flask to 2×T175 flasks until 70-80% density (medium color orange/slightly yellowish).

Cell Adaptation to Serum-Free Condition and Antibody Production Method Using T175 Flask:
6. Harvest the cells from both T175 flasks and pellet at 1000 rpm.
7. From each T175 flask remove 50% of the media (30 ml) and resuspend the cells. Then transfer the suspension back to the flask and add 30 ml of SERUM-FREE MEDIUM. Thus, FBS is reduced to 5%.
8. Adapt the cells in this 5% FBS low-serum medium for 16 to 48 hours depending on how cells grow in the medium. Note: Hybridomas should look healthy before being adapted.
9. Collect the cell suspension, pellet the cells and resuspend in 15 ml of SERUM-FREE MEDIUM.
10. Count cells.

Antibody Production Method Using Integra Flasks:
11. Inoculate 20-30 million cells resuspended in 15 ml of SERUM-FREE MEDIUM containing 1 mg/ml sterile bovine serum albumin (BSA: Sigma Aldrich cat. #A9576-50ML) to the cell compartment of a 1-Liter Integra flask.
12. Add 800 ml of SERUM-FREE MEDIUM without BSA to the nutrient compartment.
13. Culture for 10-14 days.
14. Change the media in the nutrient compartment.
15. Culture for another 7-10 days and harvest the cell suspension (approx. 15 ml) in the cell compartment as described below.
16. Rinse cell compartment once or twice with 15 ml of SERUM-FREE MEDIUM.
17. Inoculate another 20-30 million cells prepared as in steps 1 through 10 and resuspended in 15 ml of SERUM-FREE MEDIUM containing 1 mg/ml sterile bovine serum albumin to the cell compartment of the same 1-Liter Integra flask.
18. Add 800 ml of SERUM-FREE MEDIUM without BSA to the nutrient compartment.
19. Culture for 10-14 days.
20. Change the media in the nutrient compartment.
21. Culture for another 7-10 days and harvest the cell suspension (approx. 20 ml) in the cell compartment as described below.

To harvest the monoclonal antibody:
22. Harvest cell suspension.
23. Spin the suspension at 3000 rpm for 15 minutes, discard cell pellet and keep supernatant.
24. Spin the supernatant again to get rid of all cell debris.
25. Measure IgG concentration and test specificity by customer assays. Check IgG purity by SDS PAGE.
26. Typical IgG yield with two harvesting cycles: 2-10 mgs.

Healthy Hybridomas (Round, Shiny and Homogeneous, Mitotic Cells. Some Cells May Show Differential Shape).

Antibodies Sequencing.
1. High quality RNA extraction (DNA free) from hybridoma cells
2. Synthesis of the first strand of complementary DNA (RT high fidelity)
3. Synthesis of double-stranded cDNA
4. High fidelity PCR using degenerate primers flanking the variable region of heavy and light chains.
5. Direct sequencing of uncloned PCR products (double-strand sequencing) and reconstitution of the complete cDNA sequence
6. Translation of the obtained sequences
7. Validation of the peptide structure
8. Validation of the DNA sequence Example 2. Validation of Antibodies Immunohistochemistry Formalin-fixed and paraffin-embedded lymphoid tissue and cell pellet sections (3 m for all) were stained for IL4I1 using clone A-3 at 1.56 µg/mL or clone D-5 at 0.45 µg/mL using an indirect immunoperoxidase method (EnVisionSystem; DakoCytomation) after antigen retrieval with EDTA buffer at pH 8 in a water bath at 98° C. for 30 minutes. Images were captured with a ZEISS AXIOSKOP2 microscope (Zeiss, Oberkochen, Germany) and NEOFLUAR 100/0.1 NA optical lenses (Zeiss). Photographs were taken with a DP70 OLYMPUS camera (Olympus, Tokyo, Japan). Image acquisition was performed with OLYMPUS DP CONTROLLER 2002 software.

ELISA Test on Hybridomas Supernatants.

For single layer ELISA, 50 µL of conditioned media from HEK293 cells transfected to produce the recombinant human or mouse IL4I1 or transfected with empty vector were incubated overnight at 37° C. in a 96 well flat bottom plate. After extensive washes with Tris buffer saline solution (pH=7.5) containing 0.1% TWEEN detergent (TBST), plates were saturated with 5% bovine serum albumin (BSA) in TBST. Supernatants (1/6 dilution) from hybridoma clone A and clone D were then added for 2 h at 37° C. After washes with TBST, anti-rabbit-HRP antibodies were added (Sigma, dilution 1/160 000) and revelation was performed with AMPLEX RED substrate (excitation wavelength 544 nm/emission 590 nm) using an OPTIMA plate reader (BMG Labtech).

For sandwich ELISA, 96 well flat bottom plates were saturated overnight with an anti-IL4I1 antibody (directed to the N-terminal region) produced by the inventors in hen. The next day, after extensive washes with TBST, the conditioned media were added for 2 h at 37° C. After washes with TBST, each clone (A-3 or D-5) was added at a dilution of 1:2000 and the revelation was performed as above.

Western Blots.

HEK293 cells transfected with inducible hIL4I1 cDNA or empty vector were treated with tetracyclin for 48 h. After a PBS wash, cells were resuspended in 1× Laemmli buffer containing COMPLETE MINI® protease inhibitors and phosphatase inhibitors (Roche, France) and boiled for 5 min. Proteins were separated by SDS-PAGE and transferred to PVDF membranes. Supernatant for hybridoma clones A and D were used as primary antibodies, followed by anti-rabbit- HRP secondary antibodies. Revelation was performed using LUMINATA CRESCENDO® substrate from Millipore (Guyancour, France). Images were captured with a CCD camera (AUTOCHEMI system, UVP, UK) and LABWORKS software.

Immunoprecipitation.

Clone D was tested for its immunoprecipitation capacity of the recombinant human IL4I1 protein. HEK293 cells stably transfected with a vector expressing the human myc-tagged IL4I1 under the tetracycline operator or empty vector controls were used. IL4I1 expression was induced by 1 µg/mL of tetracycline. IL4I1-expressing cells and control cells were lysed in a Tris buffer containing 0.1% triton×100 and COMPLETE MINI® protease inhibitors and phosphatase inhibitors (Roche, France). Lysates (300 µL) were immunoprecipitated overnight at 4° C. with 6 µL of the hybridoma supernatant of clone D, followed by 50 µL protein A/G agarose separation for 2 h at 4° C. After elution in 30 µL of Laemmli sample buffer, 15 µL of the immunoprecipitates and 10 µL of the initial lysates (inputs) were separated on a 10% SDS-PAGE and blotted onto PVDF. Blots were revealed with an anti-myc antibody (clone 9E10 from Sigma, dilution 1:5000) followed by revelation using an anti-mouse substrate conjugated to HRP (from Sigma, dilution 1:80 000) and LUMINATA CRESCENDO® from Millipore. Images were captured with a CCD camera (AUTOCHEMI system, UVP, UK) and LABWORKS software.

Flow Cytometry.

Cells ($5 \times 10^6$) were permeabilized using the FIXPERM kit from eBioscience, according to manufacturer's instructions. Cells were then incubated at 4° C. for 30 minutes with increasing doses of purified IgG from clone D-5 or A-3 diluted in PBS containing 1% FCS or a 0.05 µg of rabbit IgG (isotype control). After washing in PBS containing 1% FCS, cells were incubated with a secondary antibody recognizing the rabbit Fc portion coupled to ALEXA FLUOR 488 dye (Molecular Probes). Data were acquired on a CYAN flow cytometer (Dako) and analyzed using the FLOWJO software.

Results

The supernatants from the selected hybridomas A and D and/or purified IgG from the selected subclones derived from these hybridomas (A-3 and D-5) have been tested for their capacity to recognize the IL4I1 protein (mouse and/or human) by different techniques (see arrow in FIGS. 2A to 2L). Both IgG A-3 and D-5 recognize the human IL4I1 enzyme produced by recombinant HEK cells and human lymph nodes after immunohistochemistry (FIG. 2 A to H). They are also able to recognize the murine protein by immunohistochemistry, although the A-3 clone seems to have a higher background (FIG. 2 I to L). Both clones recognize the denatured human IL4I1 protein in WB (FIG. 3A). Only clone D was tested for its ability to immunoprecipitate the human IL4I1 enzyme (FIG. 3B). The two clones have been tested in techniques that maintain the native structure of the protein, i. e. flow cytometry and ELISA (FIGS. 4, 5 & FIGS. 6A to 6C). In single layer ELISA (FIG. 4), both clones strongly recognize the human protein with similar efficiency. The murine protein is much less efficiently recognized, with the D clone slightly more efficient. The detection of the human protein has been also tested in sandwich ELISA using a hen polyclonal capture antibody against the N-terminal part of the protein (FIG. 5). In this assay, the sensitivity was superior with clone A-3 in comparison to clone D-5. Finally, clone A-3 had also a superior sensitivity in the detection of the human protein by flow cytometry (FIGS. 6 A & B). In contrast, the murine protein was only detected by clone D-5, but with poor sensitivity (FIG. 6 C).

TABLE 8

IL4I1 detection by single layer ELISA. Human (hIL4I1) and mouse (mIL4I1) IL4I1 recombinant proteins were absorbed on 96 well plates and revealed using clone A hybridoma supernatant or clone D hybridoma supernatant (dilution 1:6), followed by amplification with anti-rabbit HRP antibody and revelation with a fluorometric substrate.

| AB | Control | | Human IL4I1 | | Mouse IL4I1 | |
|---|---|---|---|---|---|---|
| Control | 594 | 6737 | 1307 | 40 | 6837 | 24 |
| D | 647 | 653 | 23249 | 23180 | 4144 | 4718 |
| A | 1425 | 664 | 20771 | 20949 | 1219 | 2361 |

TABLE 9

Efficacy of clones to recognize IL4I1 in Western blot (WB), immunohistochemistry (IHC), flow cytometry (FC) and sandwich ELISA assays.

| Human | | | | Mouse | | | |
|---|---|---|---|---|---|---|---|
| WB | IHC | FC | ELISA | WB | IHC | FC | ELISA |
| Clone A and/or subclone A-3 | | | | | | | |
| ++ | ++ | ++ | ++ | ND | ++ | − | ++ |
| Clone D and/or subclone D-5 | | | | | | | |
| ++ | ++ | − | ++ | ND | ++ | + | + |

(++, validated; +, less sensitive; −, no specific detection; ND, not done).

The results show that the antibody of the present invention and particularly the subclone AbA-3 works better on native epitopes and work less on mouse samples. The subclone AbD-5 works better on fully or partially denatured epitopes but also in some native conditions

CONCLUSION

The two clones and subclones developed in the present invention present capacities that can be used in the detection of IL4I1 expression both in mouse and human samples. The utilization of these clones allows the identification of IL4I1-expressing cells in tissues by immunohistochemistry, the quantification of IL4I1 in biological fluids by ELISA, the numbering of IL4I1-expressing cells by flow cytometry. Accordingly, their use may be developed in routine testing to diagnose and/or to classify patients according to their IL4I1 expression in tumor samples and/or biological fluids for prognosis or treatment purposes. They also represent good tools for preclinical studies of IL4I1 expression.

REFERENCE

Flavia Castellano and Valerie Molinier-Frenkel. An Overview of L-Amino Acid Oxidase Functions from Bacteria to Mammals: Focus on the Immunoregulatory Phenylalanine Oxidase IL4I1. Molecules 2017, 22(12), 2151.

Carbonnelle-Puscian et al. The novel immunosuppressive enzyme IL4I1 is expressed by neoplastic cells of several B-cell lymphomas and by tumor-associated macrophages. Leukemia. 2009 May; 23(5):952-60.

The invention claimed is:

1. An isolated monoclonal antibody comprising:
   a heavy chain comprising variable domain CDR sequences comprising:
   (a) a H-CDR1 comprising the sequence of SEQ ID NO: 8,
   (b) a H-CDR2 comprising the sequence of SEQ ID NO: 9 or SEQ ID NO: 18, and
   (c) a H-CDR3 comprising the sequence of SEQ ID NO: 10 or SEQ ID NO: 19; and
   a light chain comprising variable domain CDR sequences comprising:

(a) a L-CDR1 comprising the sequence of SEQ ID NO: 5,
(b) a L-CDR2 comprising the sequence of SEQ ID NO: 6 or SEQ ID NO: 14, and
(c) a L-CDR3 comprising the sequence of SEQ ID NO: 7 or SEQ ID NO: 15.

2. The isolated monoclonal antibody according to claim 1, wherein:
the variable domain CDR sequences of the light chain consist of SEQ ID NO: 5 for L-CDR1, SEQ ID NO: 6 for L-CDR2 and SEQ ID NO: 7 for L-CDR3; and
the variable domain CDR sequences of the heavy chain consist of SEQ ID NO: 8 for H-CDR1, SEQ ID NO: 9 for H-CDR2 and SEQ ID NO: 10 for H-CDR3.

3. The isolated monoclonal antibody according to claim 1, wherein:
the variable domain CDR sequences of the light chain consist of SEQ ID NO: 5 for L-CDR1, SEQ ID NO: 14 for L-CDR2 and SEQ ID NO: 15 for L-CDR3; and
the variable domain CDR sequences of the heavy chain consist of SEQ ID NO: 8 for H-CDR1, SEQ ID NO: 18 for H-CDR2 and SEQ ID NO: 19 for H-CDR3.

4. A device comprising the isolated monoclonal antibody according to claim 1 immobilized on a support.

5. The device of claim 4, wherein the support is a membrane, a slide, a microarray, a chip, a microbead or a quartz prism.

6. A kit comprising the isolated monoclonal antibody according to claim 1.

7. The kit according to claim 6 further comprising at least one reagent for performing or detecting an immune reaction.

8. An isolated monoclonal antibody produced from the hybridoma cell available under CNCM deposit number I-5355.

\* \* \* \* \*